US012048603B2

(12) United States Patent
Clark

(10) Patent No.: US 12,048,603 B2
(45) Date of Patent: Jul. 30, 2024

(54) METHODS AND DEVICES FOR CLOSING A SPACE BETWEEN TEETH

(71) Applicant: David J. Clark, Tacoma, WA (US)

(72) Inventor: David J. Clark, Tacoma, WA (US)

(73) Assignee: David J. Clark, Tacoma, WA (US)

( * ) Notice: Subject to any disclaimer, the term of this patent is extended or adjusted under 35 U.S.C. 154(b) by 69 days.

(21) Appl. No.: 16/648,765

(22) PCT Filed: Sep. 19, 2018

(86) PCT No.: PCT/US2018/051784
§ 371 (c)(1),
(2) Date: Mar. 19, 2020

(87) PCT Pub. No.: WO2019/060436
PCT Pub. Date: Mar. 28, 2019

(65) Prior Publication Data
US 2020/0246114 A1 Aug. 6, 2020

Related U.S. Application Data

(60) Provisional application No. 62/560,504, filed on Sep. 19, 2017.

(51) Int. Cl.
A61C 19/05 (2006.01)
A61C 5/85 (2017.01)
A61C 9/00 (2006.01)
A61C 13/15 (2006.01)

(52) U.S. Cl.
CPC ............ A61C 19/05 (2013.01); A61C 5/85 (2017.02); A61C 9/0053 (2013.01); A61C 19/004 (2013.01); A61C 2201/002 (2013.01)

(58) Field of Classification Search
CPC .... A61C 5/85; A61C 5/80; A61C 5/88; A61C 2201/002
See application file for complete search history.

(56) References Cited

U.S. PATENT DOCUMENTS 3,482,314 A * 12/1969 Tofflemire ............... A61C 5/85
433/39
4,129,946 A * 12/1978 Kennedy ................... A61C 5/77
433/37

(Continued)

FOREIGN PATENT DOCUMENTS

CN 1317953 A 10/2001
CN 103687568 A 3/2014
(Continued)

OTHER PUBLICATIONS

FR278896A1 Measuring wedge for gap between teeth is made from wood with graduated markings, Aug. 4, 2000. [retrieved on Dec. 6, 2021], Translation retrieved from: Espacenet. (Year: 2000).*

(Continued)

Primary Examiner — Cris L. Rodriguez
Assistant Examiner — Courtney N Huynh
(74) Attorney, Agent, or Firm — Quarles & Brady LLP

(57) ABSTRACT

In a method for closing a space between a first tooth and a second tooth, a pair of dental matrices is used. The pair of dental matrices is selected using a matrix selection tool, such as a gauge having a distal end section with color coded sections.

16 Claims, 22 Drawing Sheets

(56) References Cited

U.S. PATENT DOCUMENTS

| | | | |
|---|---|---|---|
| 4,305,707 A * | 12/1981 | Shimenkov | A61C 5/85 433/40 |
| 4,601,662 A * | 7/1986 | Galler | A61C 5/82 433/226 |
| 4,664,627 A * | 5/1987 | Kyotani | G01B 3/30 433/72 |
| 4,704,087 A | 11/1987 | Dragan | |
| 4,718,849 A | 1/1988 | von Weissenfluh | |
| 4,959,014 A | 9/1990 | Sheridan | |
| 5,044,951 A | 9/1991 | Sheridan | |
| 5,244,386 A * | 9/1993 | Angelo, Jr. | A61C 19/043 433/140 |
| 5,318,446 A | 6/1994 | Slone | |
| 5,385,155 A | 1/1995 | Kittelsen et al. | |
| 5,423,677 A * | 6/1995 | Brattesani | A61C 19/043 433/141 |
| 5,730,592 A * | 3/1998 | Meyer | A61C 5/85 433/39 |
| 5,823,773 A * | 10/1998 | Brysch | A61C 19/00 433/229 |
| 6,241,519 B1 * | 6/2001 | Sedelmayer | A61C 19/04 433/141 |
| 6,280,187 B1 | 8/2001 | Slone | |
| 8,393,897 B2 | 3/2013 | Clark | |
| 8,454,365 B2 | 6/2013 | Boerjes | |
| 9,208,531 B2 | 12/2015 | Boerjes | |
| 2002/0172920 A1 | 11/2002 | Bills | |
| 2006/0019217 A1 | 1/2006 | Yates | |
| 2007/0154860 A1 | 7/2007 | Kerle | |
| 2008/0064000 A1 | 3/2008 | Clark | |
| 2009/0208896 A1 * | 8/2009 | Clark | A61C 5/50 433/215 |
| 2012/0164594 A1 | 6/2012 | Pieroni | |
| 2014/0343614 A1 | 11/2014 | Johnson | |
| 2015/0182301 A1 | 7/2015 | Hegland | |
| 2016/0051348 A1 | 2/2016 | Boerjes | |
| 2017/0119499 A1 | 5/2017 | Clark | |

FOREIGN PATENT DOCUMENTS

| | | | |
|---|---|---|---|
| FR | 278896 A1 * | 8/2000 | ............. A61C 19/00 |
| WO | 9737612 | 10/1997 | |
| WO | WO-2008037250 A1 * | 4/2008 | ............. A61C 5/125 |
| WO | 2015187927 A1 | 12/2015 | |
| WO | 2016183360 A1 | 11/2016 | |

OTHER PUBLICATIONS

Preformed Matrix System Application Procedures. [online]. Denovo, 2017 [retrieved on Dec. 14, 2021]. Retrieved from the Internet: <URL:https://denovodental.com/app/uploads/2015/11/Matrix-Band-Instructions1.pdf>. (Year: 2017).*

2013-14 Product Catalog Matrix Selection guide. Product catalog [online]. Bioclear, 2013 [retrieved on May 18, 2023]. Retrieved from the Internet: <URL: https://www.sklep.profident.pl/product/attachment/8ad27d480cf10e1bb19fa0ec1fab1360/pl_PL/katalog.pdf>. (Year: 2013).*

Cerny, B. 3M Filtek One Bulk Fill Restorative Scientific Presentation. On or before Sep. 13, 2017.

International Searching Authority, International Search Report and Written Opinion for application PCT/US2018/051784. Mailed on Feb. 22, 2019.

Kim, J. et al. Full-Mouth Black Triangle Treatment Protocol. Dentristytoday.com Aug. 2017.

C.E.J. Inc. Contact Pro 2 Instruction Sheet. Brochure. May 2, 2008.

Slone, C. E. "New instrumentation and technique for obtaining consistent interproximal contacts of direct Class II composite restorations." Practical periodontics and aesthetic dentistry: PPAD 6.5 (1994): 15-20.

European Patent Office. Extended European Search Report for application 18857859.5. Mailed on Dec. 23, 2020. 7 pages.

Machine Translation of CN1317953A.

Machine Translation of CN 103687568A.

* cited by examiner

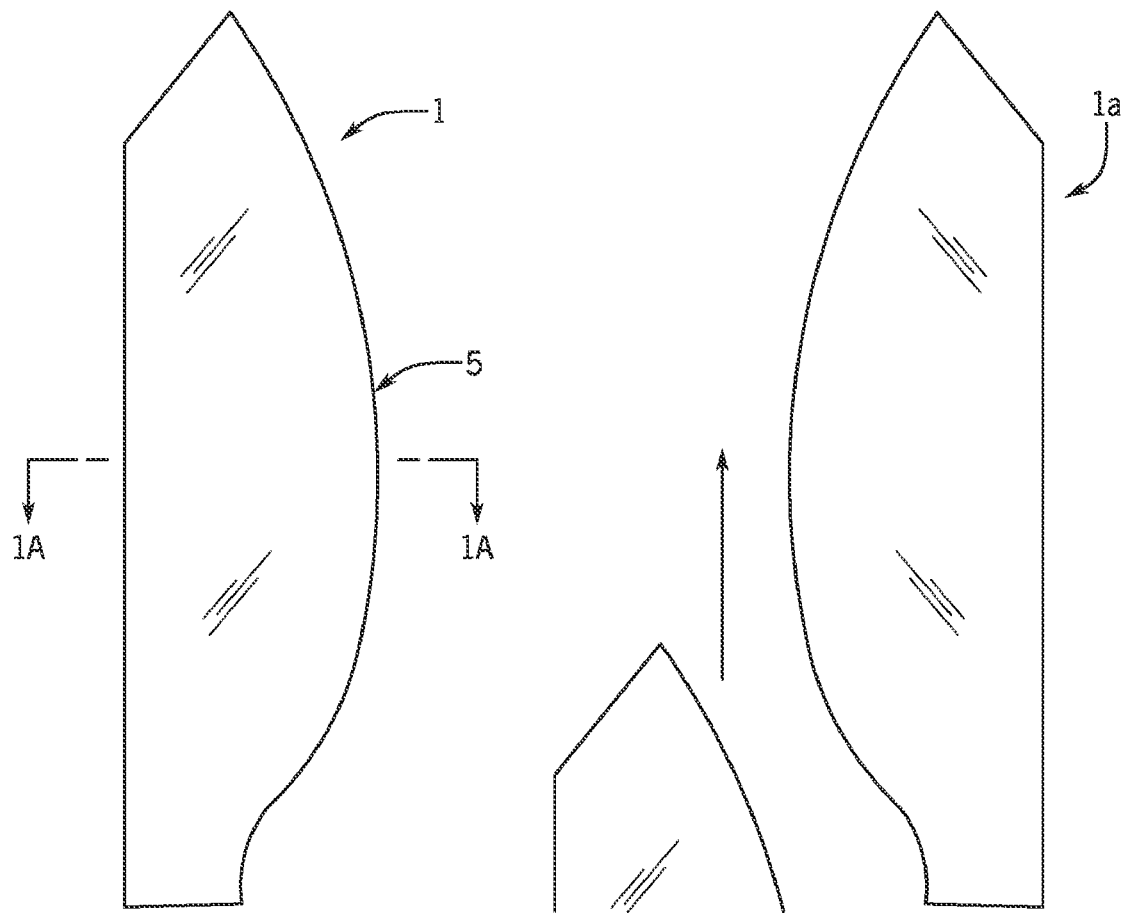
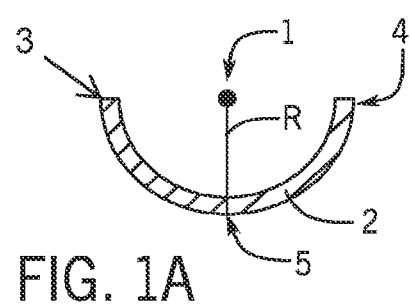
FIG. 1
PRIOR ART
FIG. 1A
FIG. 2
PRIOR ART

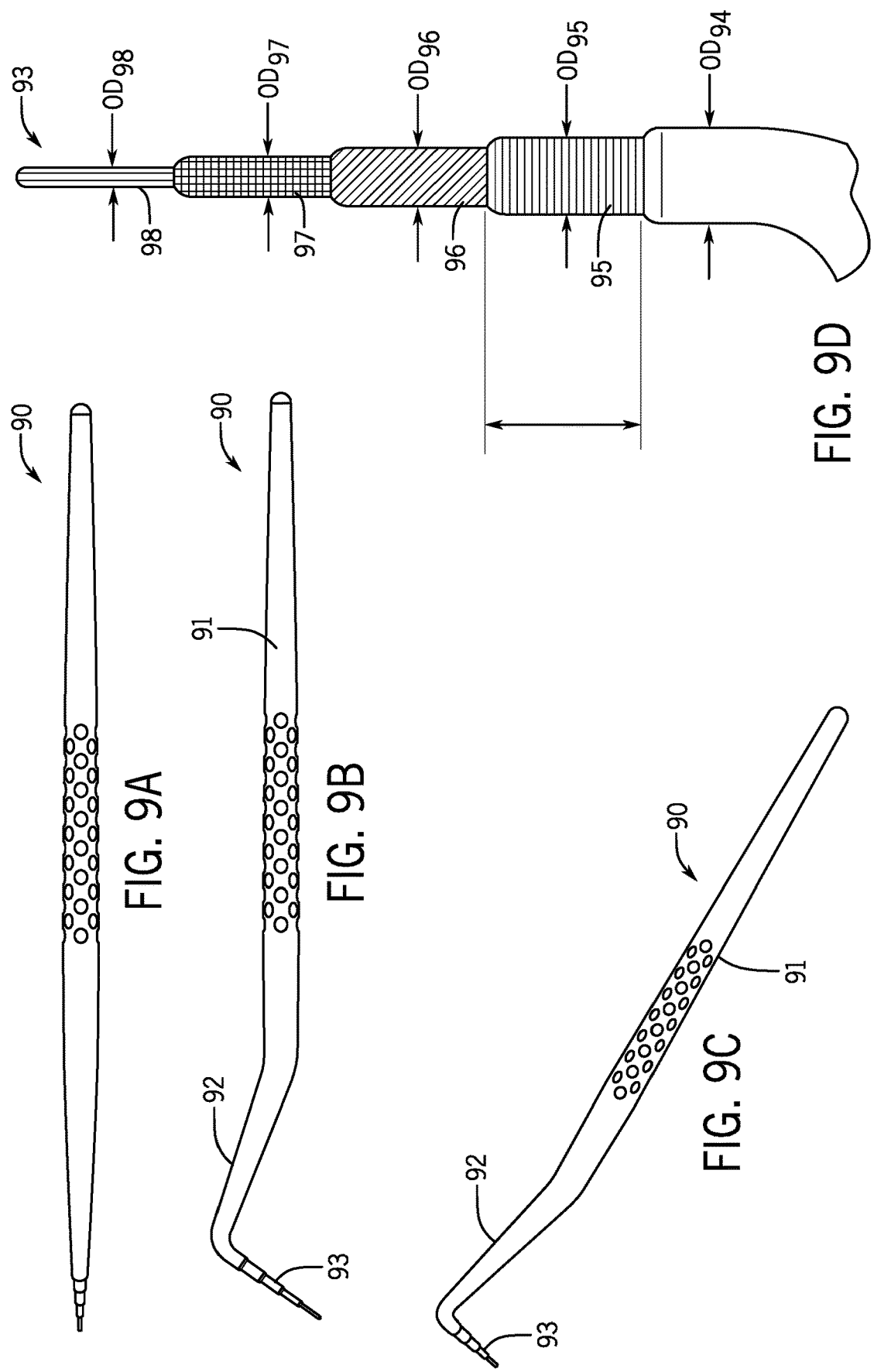

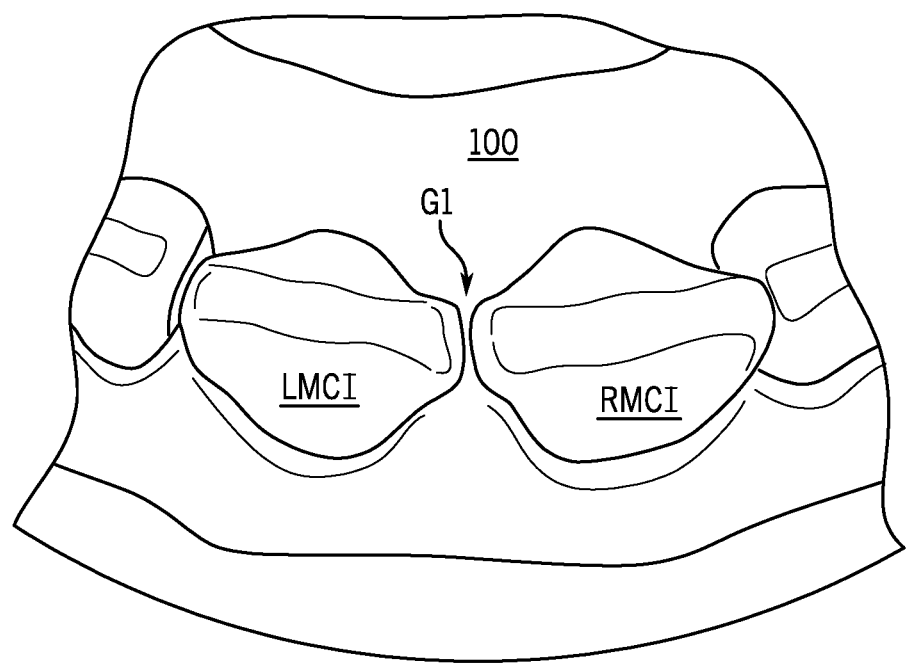
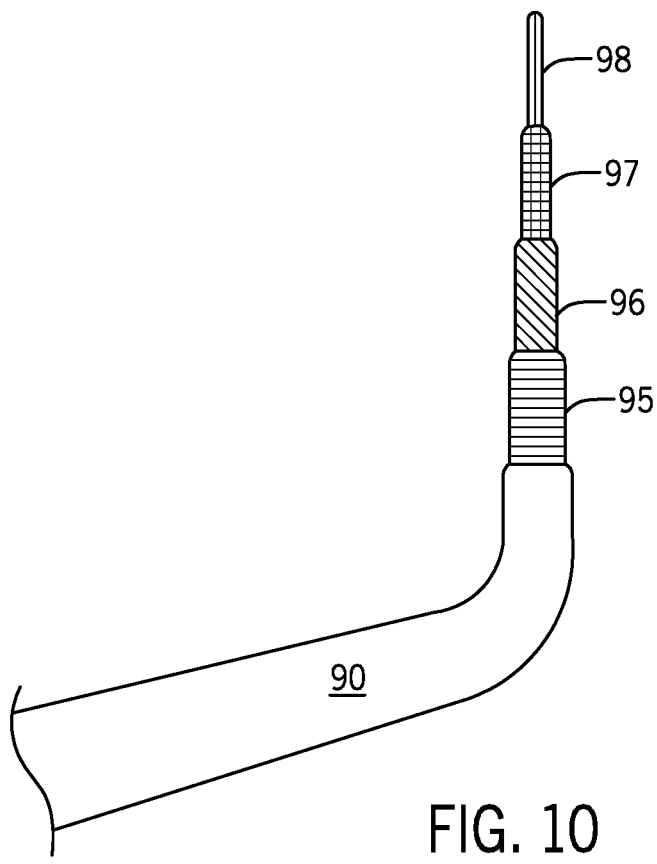
FIG. 10

METHODS AND DEVICES FOR CLOSING A SPACE BETWEEN TEETH

CROSS-REFERENCES TO RELATED APPLICATIONS

This application represents the national stage entry of PCT/US2018/051784 filed Sep. 19, 2018, which claims the benefit of U.S. Provisional Patent Application 62/560,504, filed Sep. 19, 2017, both of which are incorporated by reference herein in their entirety for all purposes.

STATEMENT REGARDING FEDERALLY SPONSORED RESEARCH

Not Applicable.

BACKGROUND OF THE INVENTION

1. Field of the Invention

This invention relates to methods and devices for closing a space between teeth and/or papilla regeneration.

2. Description of the Related Art

Gaps or "diastemas" can be present between the teeth for a variety of reasons. These include genetic and ethnic trends where there is a tooth-jaw discrepancy wherein the teeth are too small for the jaws or jaws too large for the tooth size. It is also common for the gums to recede over time creating black triangles or spaces referred to as gingival diastemas. Also, it has been reported that almost 40% of adult orthodontic treatments result in black triangles, which patients may consider a greater aesthetic issue than crowded teeth.

Black triangles have many etiologies including: (i) decreased interproximal bone height from periodontal disease, attachment loss, periodontal surgery, or trauma; (ii) excessive embrasure space and deficient papilla form affected by root angulation, interradicular distance, crown form, and distance between alveolar bone and interproximal contact; (iii) patients' biologic width and inherent or thinning gingival biotype; and (iv) other: age, patient habits, iatrogenic issues. In the modern era of cosmetically aware patients, dentists are often asked to close small and large diastemas.

The question of how to treat open gingival embrasures, or "black triangle disease," has largely stumped dental professionals. Conventional solutions for black triangles include: (i) orthodontic extrusion, to coronally reposition interproximal bone, and subsequent enameloplasty or restoration; (ii) orthodontic repositioning of divergent roots or widely spaced roots along with enameloplasty to narrow the embrasure space and encourage gingival adaptation; (iii) interproximal bone graft; (iv) soft-tissue graft or papilla reconstruction; (v) subtractive porcelain restorations or composite bonding (white and/or pink); and (v) removable prosthesis in severely compromised cases.

Reviewing the clinical options, the reasonable choices are papilla reconstruction for limited areas or orthodontics, either alone or with restorative options. Yet, what if the defects are extensive or large; or what if orthodontics has contributed to the problem, and is no longer part of the solution? Orthodontic resolutions are limited by parameters for maintaining an aesthetic maxillary central width-to-height (W/H) ratio of 80% (±5%), aesthetically pleasing relative proportions of maxillary anteriors, and Bolton ratios for appropriate interarch relationships. Surgical options are unpredictable and may not be reasonable for extensive areas. Indirect restorations can extract a high biologic cost. Many patients are unwilling to sacrifice sound tooth structure to treat black triangles, especially if the condition can progress with age. Historically, composite bonding has been too difficult to obtain a long-term healthy and aesthetic result. Black triangles in the aesthetic zone were treated only if requested; the treatment was definitely not considered for the entire mouth.

Most of the solutions to black triangles focus on amplifying the deficient papilla in an attempt to recreate the ideal balance of pink (the soft tissue) and white (the hard tissue or restoration) aesthetics. Dental professionals strive for perfection in orthodontic treatment of children. With adults, dental professionals need a reasonable solution for a compromised clinical situation. As much as dental professionals should strive for an ideal solution, if all else fails, or if the morbidity with treatment is high, should dental professionals accept the best compromise? When considering aesthetic tolerances in dentistry, both dentists and laypersons tolerate asymmetries in pink aesthetics more than asymmetries in white aesthetics. White aesthetics seemingly trump pink aesthetics, likely due to how our eyes see more of a stark contrast. For most patients, noninvasively replacing a black triangle with something that is white (tooth colored) may be a preferable compromise over unpredictable surgical options to replace pink soft tissue.

U.S. Pat. No. 8,393,897 entitled "Methods And Devices For Diastema Closure" to David J. Clark describes unique methods and devices providing a direct restorative solution to black triangles. It is very different from traditional composite bonding in technique and results. Among other things, U.S. Pat. No. 8,393,897 provides a matrix and method to treat the esthetic, functional and health problems associated with a dental black triangle or also referred to clinically as a recessed gingival papilla. The method of U.S. Pat. No. 8,393,897 is described as placement of a matrix around the tooth with a cervical bulge that has a pronounced curvature that simultaneously broadens the contact area to lessen the space between the teeth and also to put lateral pressure on each side of the papilla. This creates a "water balloon effect" as the lateral pressure on both sides of the residual gingiva encourages the papilla to creep incisally (i.e., toward the chewing surface of the tip to form a pointed apex to fill the space vertically). If a contact is within five millimeters of the bone underneath the gingiva near the contact area, a papilla will have sufficient support to form a complete papilla. In other words, once a change is made to move the contact point by growing the volume of the tooth until the contact area is no more than five millimeters away from the underlying bone, the triangular shaped papilla will fill the space completely.

Even with the advancements provided in U.S. Pat. No. 8,393,897, there is a need for further advancement in devices and methods for diastema closure and papilla regeneration.

SUMMARY OF THE INVENTION

The foregoing needs are met by the present disclosure which provides a kit that includes a more complete and easier to use and easier to understand method to measure the size of the recessed gingival papilla space, to select appropriate shaped dental matrices for a variety of sizes and shapes of residual spatial defects. In addition, the present disclosure provides advancements to the specific shape of the dental matrix that can create a more predictable process and more predictable shapes and healthier contact areas of adjacent teeth.

In one aspect of the present disclosure, there is provided a dental matrix comprising a curved strip of material. The strip can have a length from a first end to a second end sufficient to create a form for molding a restorative material to a surface of a tooth being restored. The strip can have a side surface including a radius and an interruption in the radius with a flat area in an intermediate section of the matrix. The intermediate section is located at a contact area of the tooth being restored when the matrix is placed on the tooth being restored. As one example, the interruption in the radius can be within a range of 12 millimeters to 1 millimeter in size from a top end to a bottom end of the interruption. In another non-limiting example, the interruption in the radius can be within a range of 1.5 millimeters to 0.25 millimeters in size from a front end to a back end of the interruption. Specifically, the interruption in the radius can be approximately 4 millimeters in size from the top end to the bottom end, and the interruption in the radius can be 1.5 millimeters in size from the front end to the back end of the interruption. The interruption in the radius can be flattened in both an occlusal direction from a center of the side surface and a gingival direction from the center of the side surface. In another example, the interruption in the radius can be flattened in both a buccal direction from the center of the side surface to a lingual direction from the center of the side surface. In another non-limiting example, the matrix can include a cutaway defined by a section of a gingival edge of the strip. The gingival edge can further include a concave portion, a first convex portion, and a second convex portion in a side view, such that the section of the gingival edge of the strip corresponds in shape to a coronally directed projection of gingival papilla adjacent the tooth. The material of the dental matrix can be translucent.

In yet another aspect of the present disclosure, there is provided a kit comprising a plurality of dental matrices. The plurality of matrices can include a first matrix and a second matrix. In one example, the first matrix of the plurality of matrices can comprise a first curved strip of material. The first strip can have a length from a first end to a second end and a height from a third end to a fourth end. The length and height of the first strip can be sufficient to create a form for molding a restorative material to a surface of a tooth being restored. The first strip can have a side surface including a radius and an interruption in the radius with a flat area in an intermediate section of the first matrix. The second matrix of the plurality of matrices can comprise a second curved strip of material. The second strip can have a length from a first end to a second end and a height from a third end to a fourth end. The length and height of the second strip can be sufficient to create a form for molding a restorative material to a surface of another tooth being restored. The second strip can have a side surface including a radius and an interruption in the radius with a flat area in an intermediate section of the second matrix. The first matrix and the second matrix can have different overall sizes to fit different teeth height, teeth width, or both teeth height and teeth width to fit varying sizes and shapes of both anterior and posterior teeth, maxillary and mandibular teeth. In one non-limiting example, the first matrix and the second matrix can be tooth specific, tooth type specific, and tooth surface specific.

In another non-limiting example, the present disclosure provides a method for closing a space between a first tooth and a second tooth. The method can comprise providing the plurality of matrices, inserting a root end section of a first dental matrix into the sulcus between gingival papilla and a gingival portion of the first tooth. Thereafter, the method can include placing a composite restorative material between the first dental matrix and a surface of the first tooth, and thereafter curing the composite restorative material. The method can further comprise inserting a root end section of the second dental matrix into the sulcus between gingival papilla and a gingival portion of the second tooth. The method can further comprise placing a second composite restorative material between the second dental matrix and a surface of the second tooth and thereafter curing the second composite restorative material. The space can be selected from a diastema space, a naturally occurring space, a black triangle space, and a missing tooth space.

In another aspect of the present disclosure, there is provided a dental matrix which can have a curved strip of material. The strip can have a length from a first end to a second end sufficient to create a form for molding a restorative material to a surface of a tooth being restored. The strip can also have a side surface, which can include a radius and an interruption in the radius with a flattened area in an intermediate section of a matrix located at a contact area of the tooth being restored when the matrix is placed on the tooth being restored. In one example of the present disclosure, the flattened area can have a second radius of curvature that can be larger than a first radius of curvature of a section of the side surface adjacent the flattened area. The interruption in the radius can be within a range of 12 millimeters to 1 millimeter in size from a top end to a bottom end of the interruption. The interruption in the radius can also be within a range of 1.5 millimeters to 0.25 millimeters in size from a front end to a back end of the interruption. As a non-limiting example, the interruption in the radius can be approximately 4 millimeters in size from the top end to the bottom end of the interruption, and the interruption in the radius can be approximately 1.5 millimeters in size from the front end to the back end of the interruption. The interruption in the radius can be flattened in both an occlusal direction from a center of the side surface and a gingival direction from the center of the side surface. In another example, the interruption in the radius can be flattened in both a buccal direction from the center of the side surface to a lingual direction from the center of the side surface. In another non-limiting example, the matrix can include a cutaway defined by a section of a gingival edge of the strip. The gingival edge can further include a concave portion, a first convex portion, and a second convex portion in a side view, such that the section of the gingival edge of the strip corresponds in shape to a coronally directed projection of gingival papilla adjacent the tooth. The material of the dental matrix can be translucent.

In another aspect of the present disclosure, there is provided a kit which can comprise a plurality of matrices. The plurality of matrices can include a first matrix of the plurality of matrices can comprise a first curved strip of material. The first strip can have a length from a first end to a second end and a height from a third end to a fourth end. The length and height of the first strip can be sufficient to create a form for molding a restorative material to a surface of a tooth being restored. The first strip can have a side surface which can include a radius and an interruption in the radius with a flattened area in an intermediate section of the first matrix. The plurality of matrices can also include a second matrix of the plurality of matrices. The second matrix can further comprise a second curved strip of material. The second strip can have a length from a first end to a second end and a height from a third end to a fourth end, the length and height of the second strip being sufficient to create a form for molding a restorative material to a surface of another tooth being restored, the second strip can have a side surface which can include a radius and an interruption in the radius with a flattened area in an intermediate section of the second matrix, wherein the first matrix and the second matrix can have different overall sizes to fit different teeth, height, teeth width and both teeth height and teeth width to fit varying sizes and shapes of both anterior and posterior teeth, maxillary and mandibular teeth. The first matrix and the second matrix can be tooth specific, tooth type specific, and tooth surface specific.

As one example of the present disclosure, there is provided a method for closing a space between a first tooth and a second tooth that can comprise providing a plurality of the dental matrices. The dental matrices can include a first dental matrix of the plurality and a second dental matrix of the plurality. The method can further comprises inserting a root end section of the first dental matrix into the sulcus between gingival papilla and a gingival portion of the first tooth. Thereafter, the method can include placing a composite restorative material between the first dental matrix and a surface of the first tooth, and curing the composite restorative material. The method can further comprise inserting a root end section of the second dental matrix into the sulcus between the gingival papilla and a gingival portion of the second tooth, then placing a second composite restorative material between the second dental matrix and a surface of the second tooth, and thereafter curing the second composite restorative material. The space can be selected from a diastema space, a naturally occurring space, a black triangle space, and a missing tooth space.

In another aspect of the present disclosure, there is provided a dental matrix, wherein the dental matrix can comprise a curved strip of material. The strip can have a length from a first end to a second end sufficient to create a form for molding a restorative material to a surface of a tooth being restored. The strip can also have a side surface including a radius and an interruption in the radius with a concave area in an intermediate section of matrix located at a contact area of the tooth being restored when the matrix is placed on the tooth being restored. As one example, the interruption in the radius can be within a range of 12 millimeters to 1 millimeter in size from a top end to a bottom end of the interruption. In another non-limiting example the interruption in the radius can be within a range of 1.5 millimeters to 0.25 millimeters in size from a front end to a back end of the interruption. Specifically, the interruption in the radius can be approximately 4 millimeters in size from the top end to the bottom end, and the interruption in the radius can be 1.5 millimeters in size from the front end to the back end of the interruption. The interruption in the radius can be concave in both an occlusal direction from a center of the side surface and a gingival direction from the center of the side surface. In another example, the interruption in the radius can be concave in both a buccal direction from the center of the side surface to a lingual direction from the center of the side surface. In another non-limiting example, the matrix can include a cutaway defined by a section of a gingival edge of the strip. The gingival edge can further include a concave portion, a first convex portion, and a second convex portion in a side view, such that the section of the gingival edge of the strip corresponds in shape to a coronally directed projection of gingival papilla adjacent the tooth. The material of the dental matrix can be translucent.

In yet another aspect of the present disclosure, there is provided a kit which can comprise a plurality of dental matrices. The plurality of matrices can include a first matrix and a second matrix. In one example, the first matrix of the plurality of matrices can comprise a first curved strip of material. The first strip can have a length from a first end to a second end and a height from a third end to a fourth end. The length and height of the first strip can be sufficient to create a form for molding a restorative material to a surface of a tooth being restored. The first strip can have a side surface including a radius and an interruption in the radius with a concave area in an intermediate section of the first matrix. The second matrix of the plurality of matrices can comprise a second curved strip of material. The second strip can have a length from a first end to a second end and a height from a third end to a fourth end. The length and height of the second strip can be sufficient to create a form for molding a restorative material to a surface of another tooth being restored. The second strip can have a side surface including a radius and an interruption in the radius with a concave area in an intermediate section of the second matrix. The first matrix and the second matrix can have different overall sizes to fit different teeth height, teeth width, or both teeth height and teeth width to fit varying sizes and shapes of both anterior and posterior teeth, maxillary and mandibular teeth. In one non-limiting example, the first matrix and the second matrix can be tooth specific, tooth type specific, and tooth surface specific.

In another non-limiting example, the present disclosure provides a method for closing a space between a first tooth and a second tooth. The method can comprise providing the plurality of matrices, as described above, inserting a root end section of a first dental matrix into the sulcus between gingival papilla and a gingival portion of the first tooth. Thereafter, the method can include placing a composite restorative material between the first dental matrix and a surface of the first tooth, and thereafter curing the composite restorative material. The method can further comprise inserting a root end section of the second dental matrix into the sulcus between gingival papilla and a gingival portion of the second tooth. The method can further comprise placing a second composite restorative material between the second dental matrix and a surface of the second tooth and thereafter curing the second composite restorative material. The space can be selected from a diastema space, a naturally occurring space, a black triangle space, and a missing tooth space.

In yet another aspect of the present disclosure, there is provided a measuring gauge which can include a handle section and a distal end section connected to the handle section. The distal end section can include graduated sections with different widths, and can be dimensioned to measure a space between teeth in order to select a dental matrix for closing the space between teeth. The distal end section can be used to measure a space between teeth in order to select the dental matrix or a pair of the dental matrices. The space can be selected from a diastema space, a naturally occurring space, a black triangle space, and a missing tooth space. The widths can be in a range from 0.25 millimeters to 5 millimeters and can have an abrupt transition between sizes. The distal end section can have an even and smooth transition between widths, can be round, or triangular in cross section. The widths can be equal steps in size and can be in increments of 0.25 millimeters, 0.5 millimeters, or 1 millimeter.

In another aspect of the present disclosure, there is provided a kit which can comprise a measuring gauge and a plurality of dental matrices. The measuring gauge can further comprise a handle section, and a distal end section connected to the handle section. The distal end section can include graduated sections with different widths, wherein the gauge can include a different indicia associated with each of the widths. The plurality of dental matrices can each comprise a curved strip of material. The strip can have a length from a first end to a second end sufficient to create a form for molding a restorative material to a surface of a tooth being restored, wherein a first of the dental matrices can have a first matrix indicia corresponding to one of the different indicia of the gauge, and a second of the dental matrices can have a second matrix indicia corresponding to another of the different indicia of the gauge. In another non-limiting example, an interruption in the radius can be a flat, flattened, or concave area in an intermediate section of matrix located at a contact area of the tooth being restored when the matrix is placed on the tooth being restored. The flattened area can have a radius of curvature that is larger during the flattened section. In another non-limiting example, the first matrix indicia can be a first color, a first number, a first letter, and a first symbol and the second matrix indicia can be a second color, a second number, a second letter, and a second symbol. In another non-limiting example, the kit can further comprise a tooth chart with symbols so that a user can record each of the different widths and check off an appropriate box with a corresponding matrix of the plurality of dental matrices for each of the different widths. The first of the dental matrices can include a convex inner surface at a root crown junction that extends into a second section thereby forming a bulge for positioning adjacent a gum line of the tooth being restored for closure of a space between the tooth being restored and an adjacent tooth. The second of the dental matrices can include a convex inner surface at a root crown junction that extends into a second section thereby forming a bulge for positioning adjacent a gum line of the tooth being restored for closure of a space between the tooth being restored and an adjacent tooth, wherein the bulge of the first of the dental matrices and the bulge of the second of the dental matrices can have different sizes.

In yet another aspect of the present disclosure, there is provided a method for closing a space between a first tooth and a second tooth. The method can comprise: (i) providing a plurality of dental matrices, (ii) measuring a width of the space with a digital camera or digital scanner, (iii) choosing one of the plurality of matrices by matching the indicia to the width, (iv) inserting a root end section of the one of the plurality of matrices into the sulcus between gingival papilla and a gingival portion of the first tooth, (v) placing a composite restorative material between the one of the plurality of matrices and a surface of the first tooth, and (vi) curing the composite restorative material. Each of the plurality of dental matrices can have an indicia of size. A first matrix of the plurality of matrices can comprise a first curved strip of material. The first strip can have a length from a first end to a second end and a height from a third end to a fourth end, wherein the length and height of the first strip being sufficient to create a form for molding a restorative material to a surface of a tooth being restored. The first strip can have a side surface which can include a radius and an interruption in the radius with a flat area in an intermediate section of the first matrix. The plurality of matrices can further include a second matrix which can comprise a second curved strip of material. The second strip can have a length from a first end to a second end and a height from a third end to a fourth end, wherein the length and height of the second strip being sufficient to create a form for molding a restorative material to a surface of another tooth being restored. The second strip can have a side surface which can include a radius and an interruption in the radius with a flat area in an intermediate section of the second matrix, wherein the first matrix and the second matrix have different overall sizes to fit different teeth height, teeth width or both teeth height and teeth width to fit varying sizes and shapes of both anterior and posterior teeth, maxillary and mandibular teeth. The method can further include a software that suggests the one of the plurality of matrices. In one non-limiting example, choosing one of the plurality of matrices by matching the indicia to the width can further comprise printing or milling the one of the plurality of matrices using a milling or printing machine in a remote facility to be shipped to a user based on the width of the space measured by the camera or the scanner and a computed file created for the printing or milling, and printing or milling the one of the plurality of matrices using a chairside office printer or milling machine that makes the one of the plurality of matrices for immediate use.

In another aspect of the present disclosure, there is provided a method for overmolding or molding a dental restorative material on a tooth. The method can comprise: (i) measuring dimensions of a space adjacent the tooth with a digital camera or digital scanner, and (ii) printing or milling a dental matrix based on the dimensions to create a form for overmolding or molding the restorative material in the space. As one example, the method can further comprise steps: (iii) placing a composite restorative material between the dental matrix and a surface of the tooth, and (iv) thereafter curing the composite restorative material. Printing or milling a dental matrix based on the dimensions to create a form for overmolding or molding the restorative material in the space can further comprise printing or milling the dental matrix using a chairside office printer or milling machine that makes the matrix for immediate use.

In yet another aspect of the present disclosure, there is provided a method for restoring or adding a tooth. The method can comprise: (i) using a gauge, a digital scanner, an x-ray device, an ultrasonic device, an MRI imaging device, or another imaging device to record a shape of a tooth digitally, (ii) digitally creating a design for a new tooth to restore a broken, diseased or worn tooth or to add to a tooth for cosmetic or functional reasons, and (iii) printing or milling either chairside or remotely a dental matrix or a set of dental matrices to be placed on or around the tooth to allow injection molding and injection over-molding of the tooth.

In another aspect of the present disclosure, there is provided a measuring gauge. The gauge can comprise a handle section, and a distal end section connected to the handle section. The distal end section can include a plurality of contiguous surface sections, wherein each surface section can be dimensioned to have one of a plurality of different indicia to be used as a gauge to select an appropriate thickness of light curable flowable composite resin to be placed in a cavity preparation. Each of the plurality of different indicia can be a different color, a different number, or a different symbol. The plurality of contiguous surface sections can comprise: (i) a first surface section which can have a first longitudinal length extending from a tip of the distal end section to a proximal end of the first surface section, wherein the first longitudinal length corresponding to a depth of cure value of the light curable flowable composite resin, and (ii) a second surface section extending proximally from the proximal end of the first surface section. As one example, the plurality of contiguous surface sections can comprise: (i) a first surface section which can have a first longitudinal length extending from a tip of the distal end section to a proximal end of the first surface section, the first longitudinal length corresponding to a first depth of cure value of the light curable flowable composite resin at a first location in the cavity preparation, (ii) a second surface section extending proximally from the proximal end of the first surface section such that a second longitudinal length extending from the tip of the distal end section to a proximal end of the second surface section corresponds to a second depth of cure value of the light curable flowable composite resin at a second location in the cavity preparation, and (iii) a third surface section extending proximally from the proximal end of the second surface section.

As another non-limiting example, the present disclosure provides a method for restoration of a tooth. The method can comprise: (i) removing a portion of the tooth to form a hollow cavity preparation, (ii) inserting the distal end section of the gauge into the hollow cavity preparation until a tip of the distal end section of the gauge contacts a bottom surface of the cavity preparation, (iii) observing a location of an upper edge of the cavity preparation relative to the distal end section of the gauge and choosing one of the surface sections that is closest to the upper edge of the cavity preparation, (iv) injecting a depth of light-curable flowable composite resin into the cavity preparation based on the indicia of the one of the surface sections that is closest to the upper edge of the cavity preparation, and (v) light curing the flowable composite contained in the cavity preparation.

It is an advantage of the present invention to provide methods and devices for closing a space and/or papilla regeneration between teeth that provide rounded marginal profiles.

It is another advantage of the present invention to provide methods and devices for closing a space and/or papilla regeneration between teeth that do not compromise the root-crown architecture.

It is yet another advantage of the present invention to provide methods and devices for closing a space and/or papilla regeneration between teeth that provide for bulbousness near the gum line to fill the gingival gapping.

It is still another advantage of the present invention to provide a matrix for closing a space and/or papilla regeneration between teeth wherein the matrix has an anatomic shape in the gingival portion but then with varying levels of exaggerated profile at the root-crown junction.

It is yet another advantage of the present invention to provide a matrix for closing a space and/or papilla regeneration between teeth wherein the matrix is a sectional matrix that is specific to the anterior teeth and specifically designed for diastema closure with bonded composite filling material.

It is still another advantage of the present invention to provide a matrix for closing a space and/or papilla regeneration between teeth wherein the matrix is a matrix specifically designed for the closure of diastema (tooth gapping).

It is yet another advantage of the present invention to provide a matrix for closing a space and/or papilla regeneration between teeth wherein the matrix is a sectional matrix that is tooth specific.

It is still another advantage of the present invention to provide a matrix for closing a space and/or papilla regeneration between teeth wherein the matrix is a sectional matrix that is tooth and surface specific with an exaggerated root-crown profile.

It is yet another advantage of the present invention to provide devices for closing a space and/or papilla regeneration between teeth with precise fit of custom matrices that allows the matrices to be used without interdental wedges or elastic separators or spacers.

It is still another advantage of the present invention to provide methods and devices for closing a space and/or papilla regeneration between teeth that allow for formation of aesthetically pleasing papilla between adjacent teeth after diastema closure.

It is yet another advantage of the present invention to provide methods and devices for closing a space and/or papilla regeneration between teeth that avoid subsequent deterioration in periodontal health after diastema closure.

It is still another advantage of the present invention to provide a matrix for closing a space and/or papilla regeneration between teeth wherein the matrix can slide to the depth of the sulcus without lacerating the tissue.

These and other features, aspects, and advantages of the present invention will become better understood upon consideration of the following detailed description, drawings and appended claims.

BRIEF DESCRIPTION OF THE DRAWINGS

FIG. 1 is a front view of a dental matrix used for diastema closure.

FIG. 1A is a cross-sectional view of the dental matrix of FIG. 1 taken along line 1A-1A of FIG. 1.

FIG. 2 is a front view of a pair of dental matrices of FIG. 1 being mated for use in diastema closure.

FIG. 9A is a top view of a matrix selection tool of the present invention.

FIG. 9B is a side view of the matrix selection tool of FIG. 9A.

FIG. 9C is a perspective view of the matrix selection tool of FIG. 9A.

FIG. 9D is a detailed view of the distal end section of the matrix selection tool of FIGS. 9A-9C.

FIG. 10 shows a detailed view of the matrix selection tool of FIG. 9A before insertion between maxillary central incisors of a dental model.

Like reference numerals will be used to refer to like parts from Figure to Figure in the following description of the drawings.

DETAILED DESCRIPTION OF THE INVENTION

Figure 3:
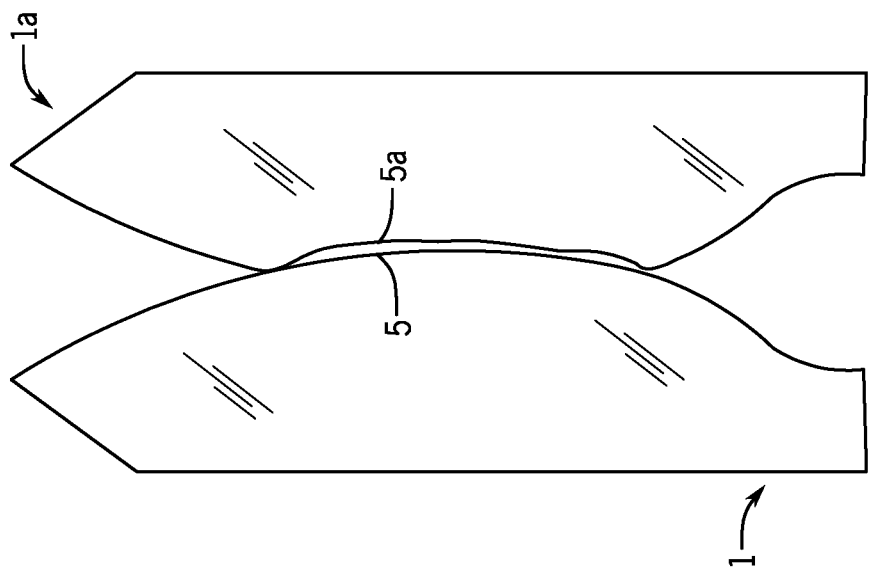
FIG. 3 is a front view of one problem that may be encountered when using a pair of dental matrices for diastema closure.

Referring to FIGS. 1 to 5, a dental matrix 1 can be used to treat the dreaded black triangle using the methods described in U.S. Pat. No. 8,393,897. Most of the time, the procedure is well done and pleases the patient and the doctor. However, there are advancements that need to be made. A front view of a single dental matrix 1 is shown in FIG. 1. The matrix 1 has a curved strip 2 of material. The strip 2 has a length from a first end 3 to a second end 4 sufficient to create a form for molding a restorative material to a surface of a tooth being restored. The strip 2 has a side surface 5 having a radius R. In FIG. 2, matrix 1 is placed on the mesial surface of a right maxillary central incisor (not shown) to pair with a second matrix 1a on the mesial surface of a left maxillary central incisor (not shown) with ideal tension when the correct curvatures happen to match the black triangle space. Identical to matrix 1, the matrix 1a has a strip with a length from a first end to a second end sufficient to create a form for molding a restorative material to a surface of a tooth being restored. The matrix 1a has a side surface 5a having a radius.

Figure 4:
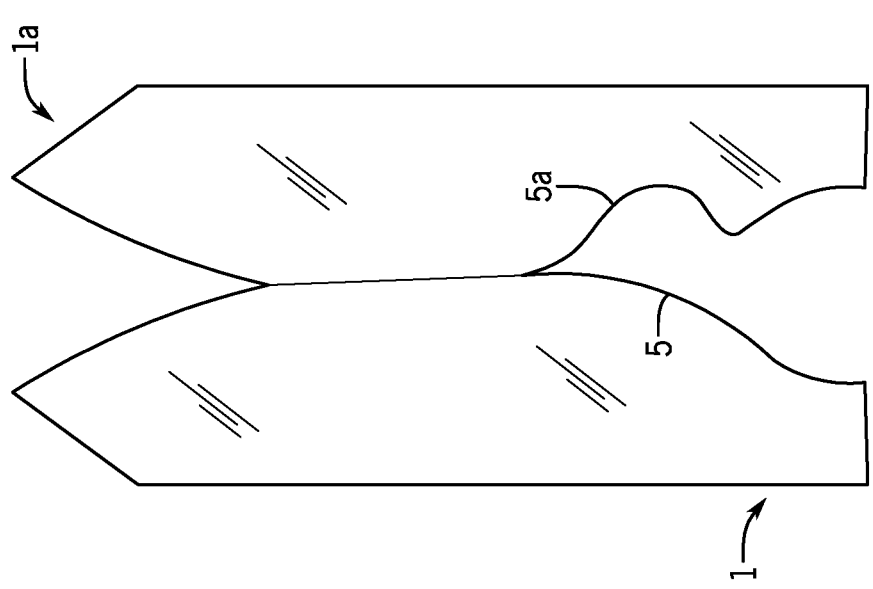
FIG. 4 is a front view of another problem that may be encountered when using a pair of dental matrices for diastema closure.
Figure 5:
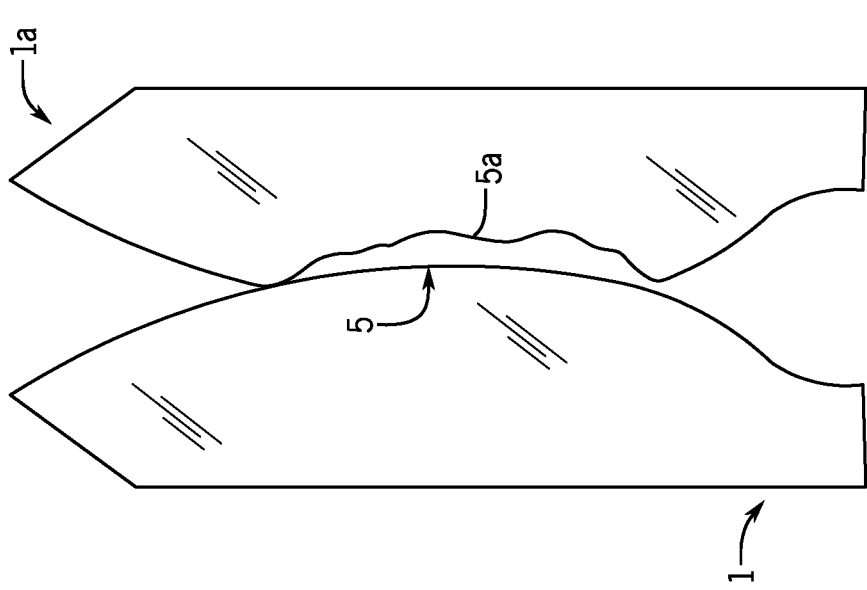
FIG. 5 is a front view of another problem that may be encountered when using a pair of dental matrices for diastema closure.

In a smaller space, the matrix 1 can "bully" the other matrix 1a, and the convexity of the side surface 5 of matrix 1 on the left crumples the side surface 5a of matrix 1a on the right in mid tooth. See FIG. 3. In FIG. 4, the matrix 1a is crumpled at a different part of the side surface 5a of the matrix 1a on the right. In FIG. 5, the matrix 1a is inverted at side surface 5a. Any of these three inadvertent wrong shapes of FIGS. 3-5 are possible with a pairing of matrix 1 and matrix 1a. When composite restorative material is placed, the material is injected in a flowable state and then solidified (i.e., polymerized) inside of the matrix and whatever shape the matrix is, becomes the resulting shape of the filling material. The resulting shape of the composite material may match the improper altered shape of the matrix 1a in the examples of FIGS. 3 to 5 and if left in place, will cause food impaction and periodontal (gum) inflammation and possible infection. The management of two convex contact areas in a thin pliable material required for light transmission (clear polymeric material, such as Mylar® polyester film used in matrices 1 and 1a, instead of stainless steel strips) is difficult clinically and is very prone to distort. It may be a challenge for the clinician when using matrices 1 and 1a. At times, a dentist may fail to identify the crumpled or inverted matrix of the pair of matrices, and only after the restorative material is polymerized does the dentist identify the problem. As a result, the final restoration will have to be drilled away and replaced, or the patient will have to live with a less than ideal health of the gums in that area.

To alleviate the problem with improperly altered shapes of a matrix, such as that shown in the examples of FIGS. 3 to 5, additional work is required to customize the matrix 1 by inserting the matrices on the teeth near the black triangle, evaluating excessive curvatures, then removing and trimming the bottom of the matrix with special micro-scissors to decrease the curvatures. Then the matrices 1 are re-inserted and checked again. Sometimes the process has to be repeated to trim the matrices again, or even to start over with new matrices if the matrix or matrices are cut too much and became too flat.

Figure 6A:
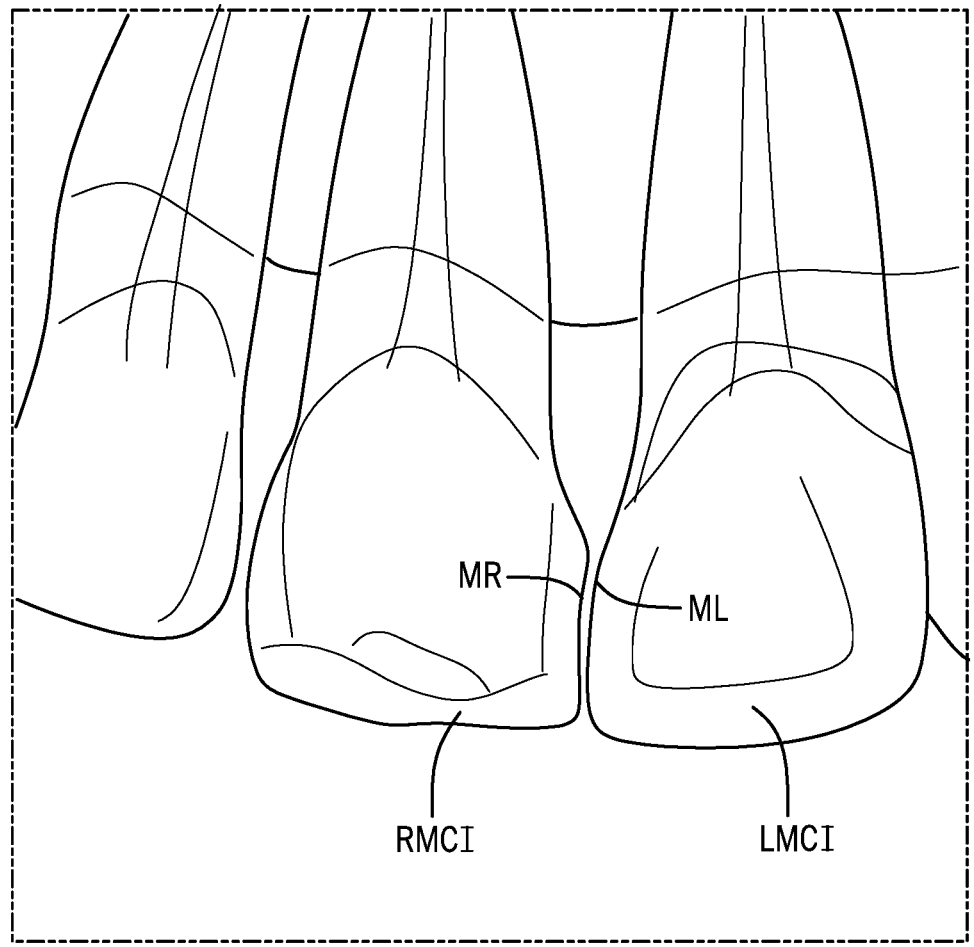
FIG. 6A is a front view of a tracing of an x-ray of a problem that may be encountered when using a pair of dental matrices for diastema closure.
Figure 6B:
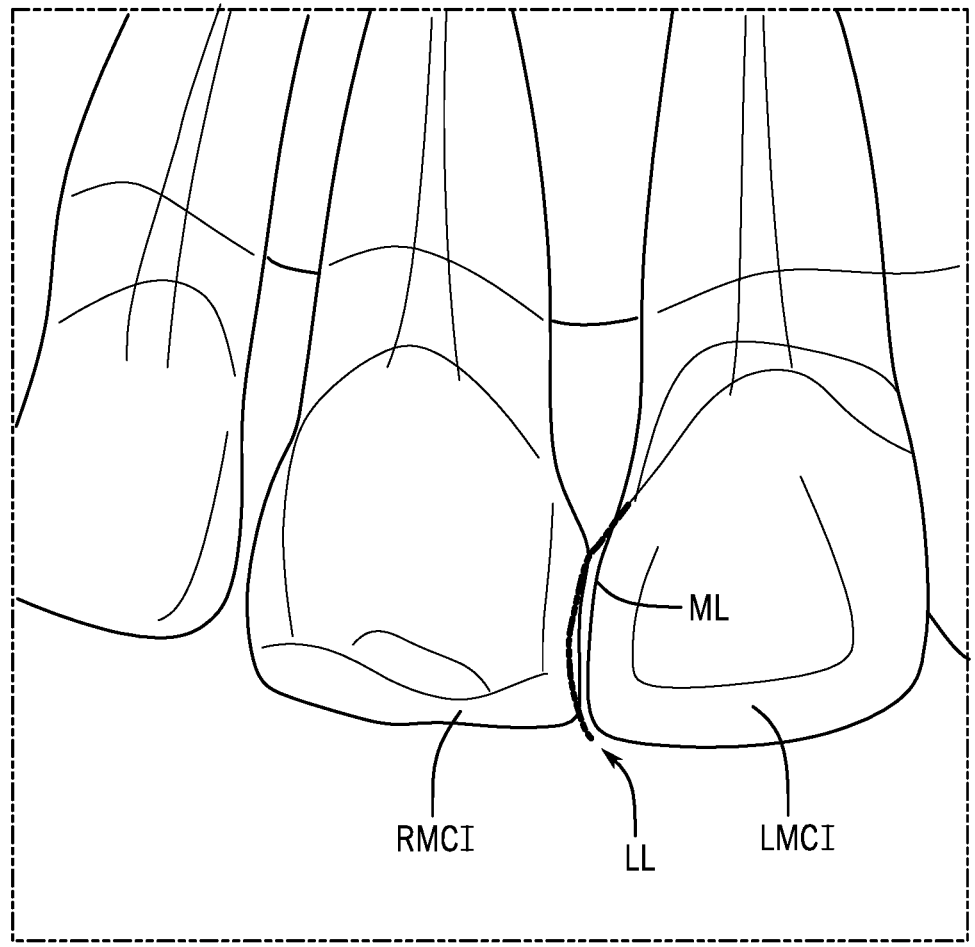
FIG. 6B is a front view of a marked tracing of the x-ray of FIG. 6A showing a problem that may be encountered when using a pair of dental matrices for diastema closure.
Figure 7:
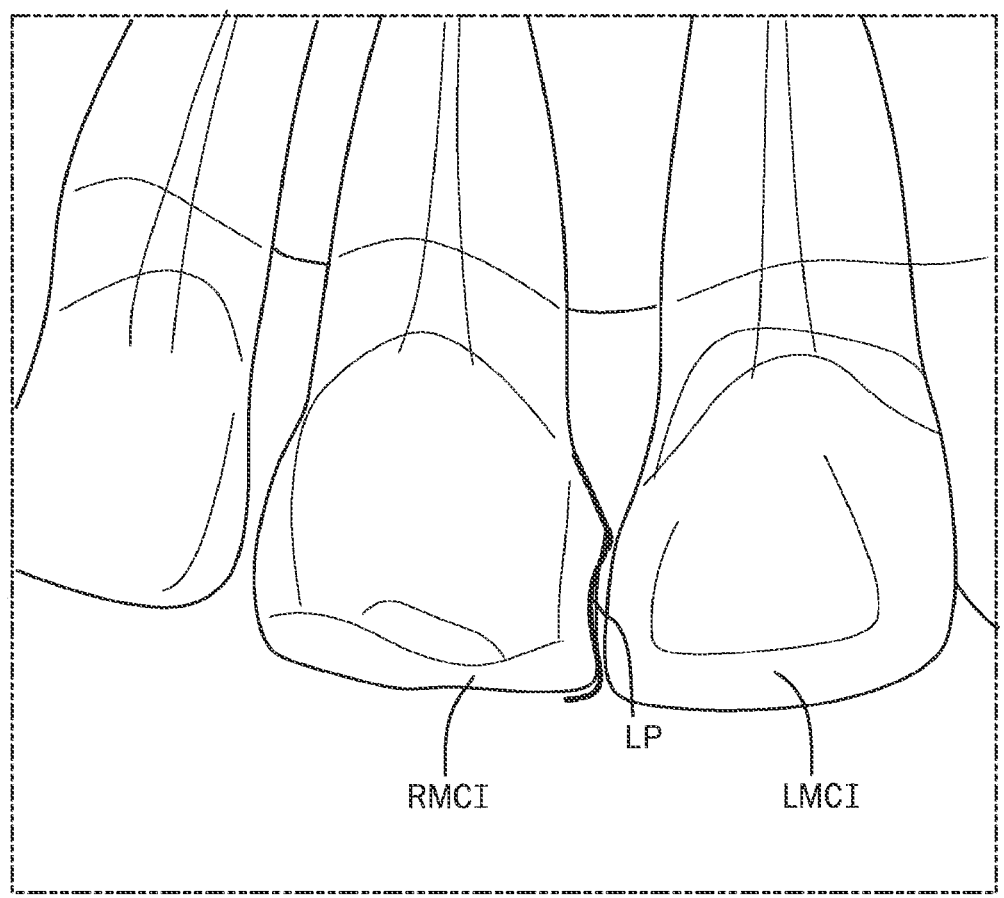
FIG. 7 is a front view of a marked tracing of the x-ray of FIG. 6A showing a problem that may be encountered when using a pair of dental matrices for diastema closure.
Figure 8A:
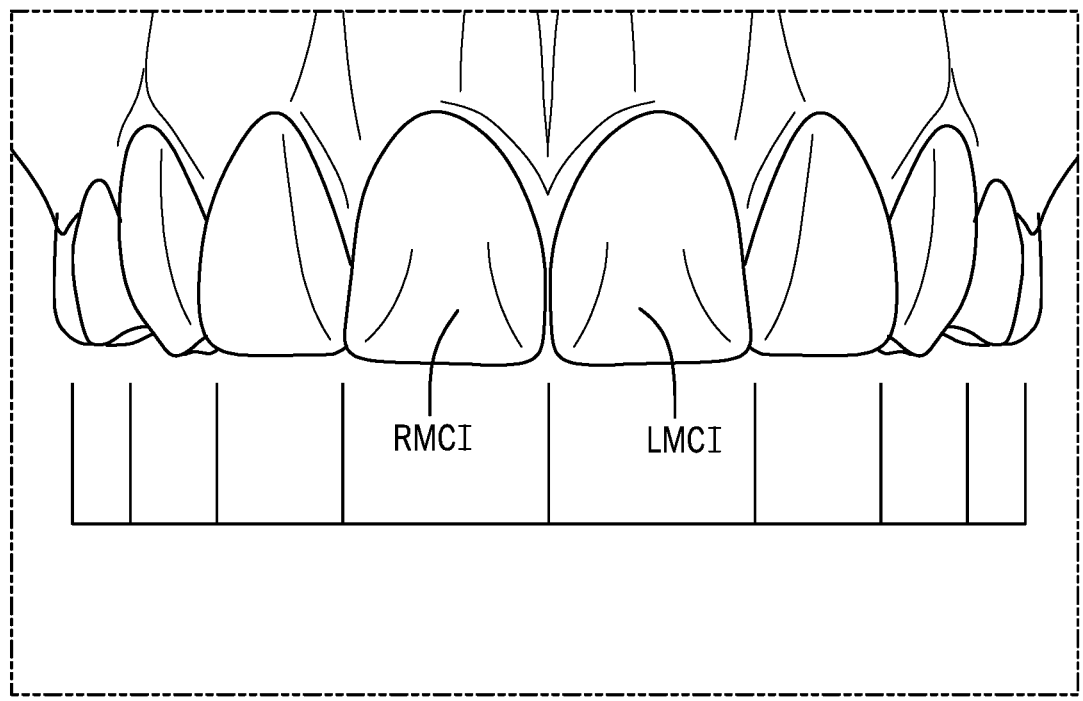
FIG. 8A is a front view showing central incisors. A golden proportion grid is shown below the teeth. The Golden Ratio represents a 1:1.618 ratio used to position the central and lateral incisors.
Figure 8B:
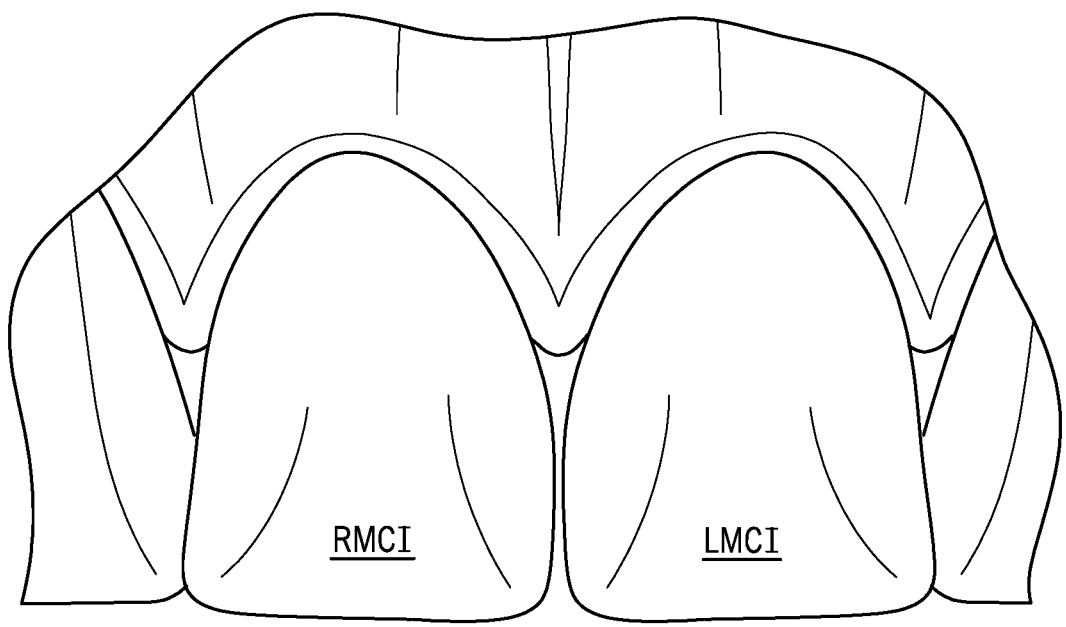
FIG. 8B is a detailed view of the teeth of FIG. 8A.

FIGS. 6A to 7 further illustrate this problem. FIGS. 6A and 6B show how an overly convex contact area inverts the other matrix and the result is the shape of the mesial side MR of the right maxillary central incisor RMCI will be concave (see line LL in FIG. 6b) and the shape of the mesial side ML of the left maxillary central incisor LMCI will include a concave region shown by line LP in FIG. 7. FIG. 7 shows how a concave contact area creates stain, bacterial accumulation and a canted (crooked) midline LP. In the case of FIG. 7, matrix problems create asymmetrical central incisor teeth (the left maxillary central incisor LMCI is wider than the right maxillary central incisor RMCI). See FIGS. 8A and 8B. This is never an acceptable outcome and the layperson easily identifies that something is wrong. For ideal esthetics, the central incisors must be mirror images of each other.

The present disclosure provides advancements that eliminate the problems identified with reference to FIGS. 1 to 8B. Among other things, the present disclosure provides: (i) a matrix selection tool (e.g., a graduated gauge) that allows the dental practitioner to select a pair of matrices dimensioned to alleviate the problem with improperly altered shapes of a matrix such as that shown in the examples of FIGS. 3 to 5; (ii) a kit including color coded paired matrices that allow the dental practitioner to avoid the problem with improperly altered shapes of a matrix such as that shown in the examples of FIGS. 3 to 5; and (iii) methods for using the matrix selection tool and the paired matrices.

Referring now to FIGS. 9A, 9B, 9C, and 9D, a graduated gauge 90 of the invention suitable for use as a matrix selection tool is shown. The graduated gauge 90 has a handle section 91, an intermediate section 92 angled 70° with respect to the handle section 91, and a distal end section 93 angled 105° with respect to the intermediate section 92. The distal end section 93 includes a first section 95 color coded blue and having a 2 millimeter outside diameter $OD_{95}$, a second section 96 color coded green and having a 1.50 millimeter outside diameter $OD_{96}$, a third section 97 color coded yellow and having a 1 millimeter outside diameter $OD_{97}$, and a fourth section 98 color coded pink and having a 0.50 millimeter outside diameter $OD_{98}$. The outside diameter $OD_{94}$ is about 2.5 millimeters.

Figure 11:
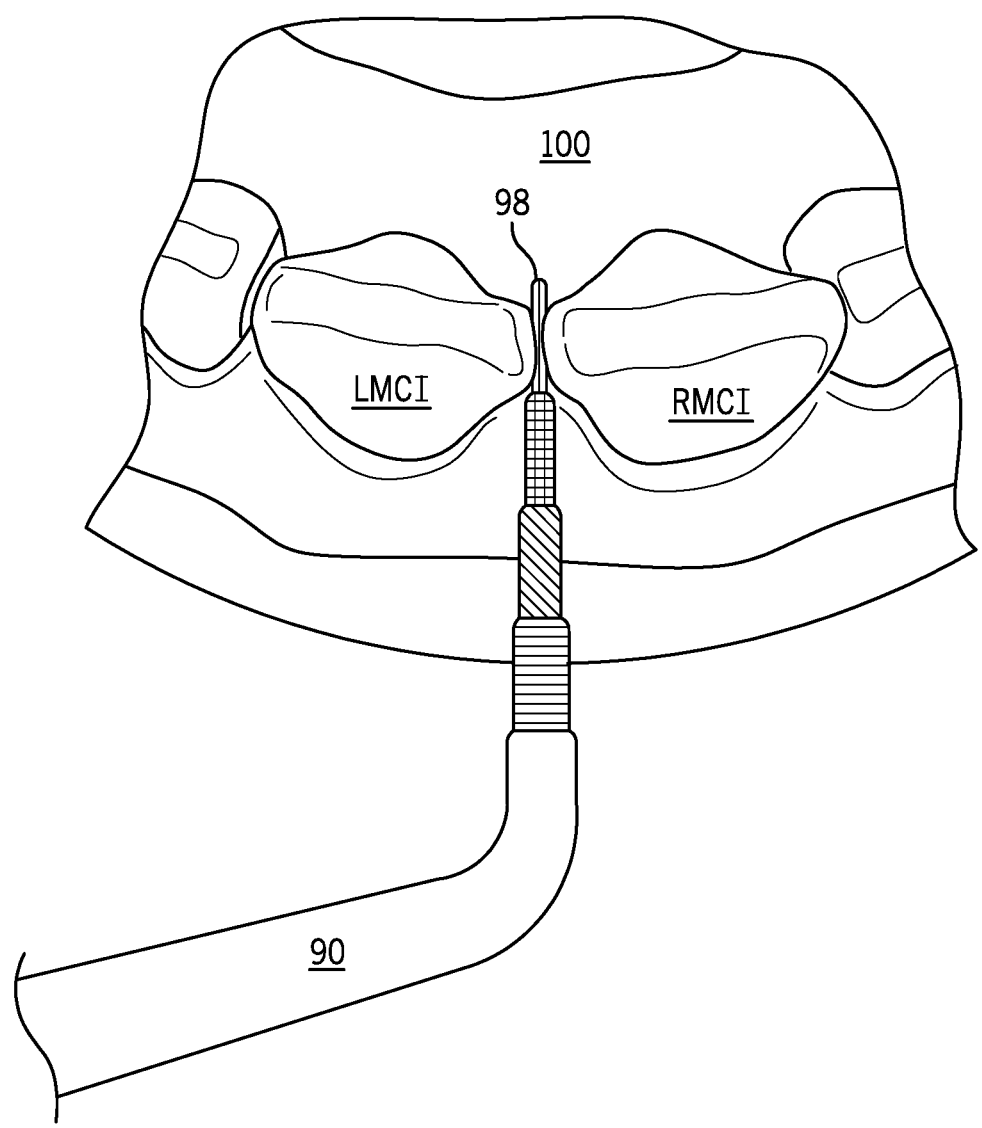
FIG. 11 shows a detailed view the matrix selection tool of FIG. 9A inserted between maxillary central incisors of a dental model illustrating measurement of the width of a first diastema.

FIGS. 10 to 22 demonstrate a method for using the graduated gauge 90 to select a pair of matrices to be used in a method for diastema closure and treating recessed gingival papilla. FIG. 10 shows the graduated gauge 90 of the invention before insertion between the right maxillary central incisor RMCI and the left maxillary central incisor LMCI of a dental model 100 including the maxillary teeth. In FIG. 11, it can be seen that that fourth section 98 (color coded pink and having a 0.50 millimeter outside diameter) of the graduated gauge 90 fits best in the gap G1 (modeling a space between teeth) between the right maxillary central incisor RMCI and the left maxillary central incisor LMCI of the dental model 100. This space can be referred to as a "pink" sized space, and in FIG. 12, the right maxillary central incisor RMCI and the left maxillary central incisor LMCI are temporarily labeled with a pink dye Dp indicating the space size. In FIG. 13, a pair of "pink" sized matrices 13, 14 are placed in back to back relationship between the right maxillary central incisor RMCI and the left maxillary central incisor LMCI. The matrices 13, 14 include pink color coded sections 13d, 14d respectively.

Still looking at FIG. 13, the clear plastic anatomical sectional matrices 13, 14 can be placed around the right maxillary central incisor RMCI and the left maxillary central incisor LMCI and maintain anatomic root adaptation contact by way of an anatomic root end section of the matrices 13,14. The matrices 13,14 are self-wedging and self-stabilizing. The outer surface of each of the maxillary central incisors is etched with liquid and/or gel phosphoric acid. Alternatively, the method can incorporate self etching resins that do not require a separate etching step with phosphoric acid; or any technique that allows a filling material to bond to dentin (cementum) and enamel. The outer surface of each of the maxillary central incisors can be reached by way of a slit in the end of the matrices 13,14, or by gently pulling the incisal portion of the matrices 13,14 away from the tooth while leaving the gingival portion of the matrices 13,14 undisturbed. The outer surface of each of the maxillary central incisors is then rinsed and dried. A lightly filled or unfilled light curable resin tooth bonding agent is then applied to outer surfaces of each of the maxillary central incisors. The resin tooth bonding agent is not light cured at this point. Resin tooth bonding agents improve composite to enamel and/or dentin bonding. However, a resin bonding agent may not be required. One example resin tooth bonding agent is available under the tradename OptiBond Solo Plus®.

A light curable flowable composite resin is then injected directly on the resin tooth bonding agent (under magnification if possible) without incorporating bubbles. A tiny amount of the light curable flowable composite resin is expressed before placement to ensure that there is no air in the cannula. The light curable flowable composite and resin tooth bonding agent are not light cured at this point. Generally, light curable flowable composite resins contain 20-25 percent less filler in the light curable polymeric material than nonflowable paste materials. Light curable flowable composite resins are available under tradenames such as Filtek™, Flow-It™, EsthetX®, Revolution®, AeliteFlo®, PermaFlo®, Dyract Flow®, Tetric®, and Heliomolar®. Light curable resins could be preferred as light cured resins can be more color stable than chemically cured resins. However, chemical cure or any type of polymerization/hardening/curing of the filling material can also be used. The use of a metallic matrix may dictate the use of a chemical cure. Also, the method is not limited to flowable composite resins with lesser filler particles. One example variation includes an initial placement of a more flowable composite first, which can include flowable composites that are made less viscous than paste composite materials by virtue of lower filler content, but also from thixotropic effect of extrusion thru a small orifice tip, heating of a highly filled paste material that has temporary decreased viscosity to allow more flow and easier placement; or any modification of the paste through chemical and filler content formulation change, temporary or transitional viscosity decrease thru heat, and or pressure and or other physical effect.

A light curable paste composite resin is then extruded onto the flowable composite resin and resin tooth bonding agent without creating air bubbles, allowing the composite resin to displace some of the lesser filled flowable composite resin and resin tooth bonding agent (under magnification if possible). Composite resins are available under tradenames such as 3M Z100™, 3M Filtek Supreme™, and Prodigy®. The next steps are burnishing, carving the anatomy and carving excess composite. There is no need to use a condenser or plugger. Immediately after using the injection molding technique, the matrices 13, 14 move nicely to close the incisal gap but continue to hug the cervical area of the teeth. The gingival sulcus itself provides stabilization. Alternatively, other products such as silicon stabilizer specific or non-specific wedges also can be used with the matrix depending on the specific case or operator preference. Wedges can press the matrix against the root of the tooth. While traditional wedges can smash the exaggerated crown-root junction profile of the matrix, certain wedges may work with delicate stabilization. If a metallic matrix or thick polymeric matrix is used, a traditional wedge will not smash the exaggerated crown-root junction profile of the matrix.

The filled preparation is then cured using a curing light such as high intensity light emitting diode (LED) lights, plasma-arc curing lights, halogen lights, and laser lights. The matrices 13, 14 are then removed, and the restored maxillary central incisors are polished with discs, strips, and rubber tipped and carbide burs. A seamless filling is achieved.

Figure 12:
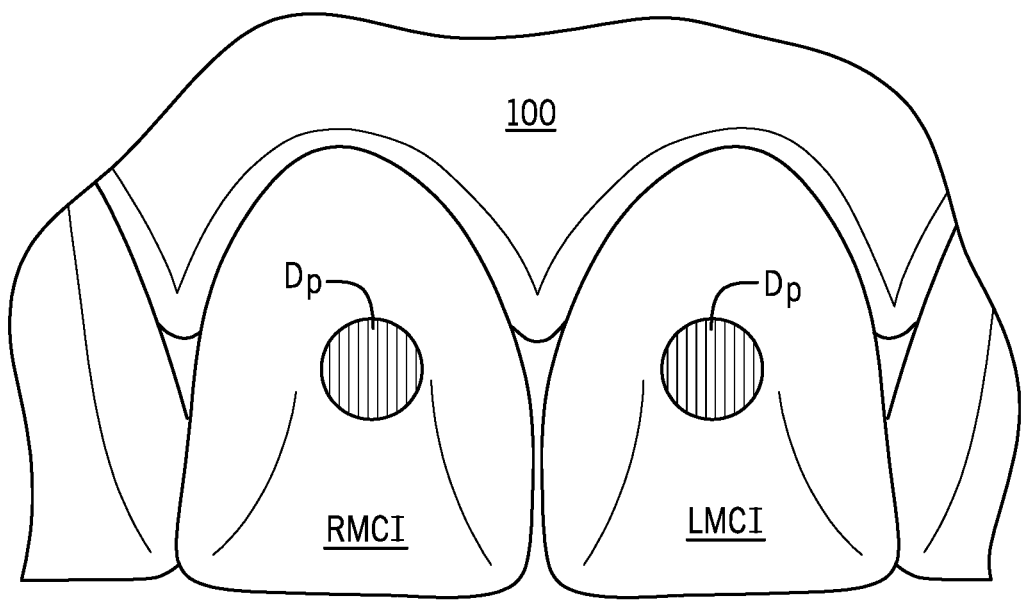
FIG. 12 shows a front view of a dental model illustrating color coding maxillary central incisors with a first color.
Figure 13:
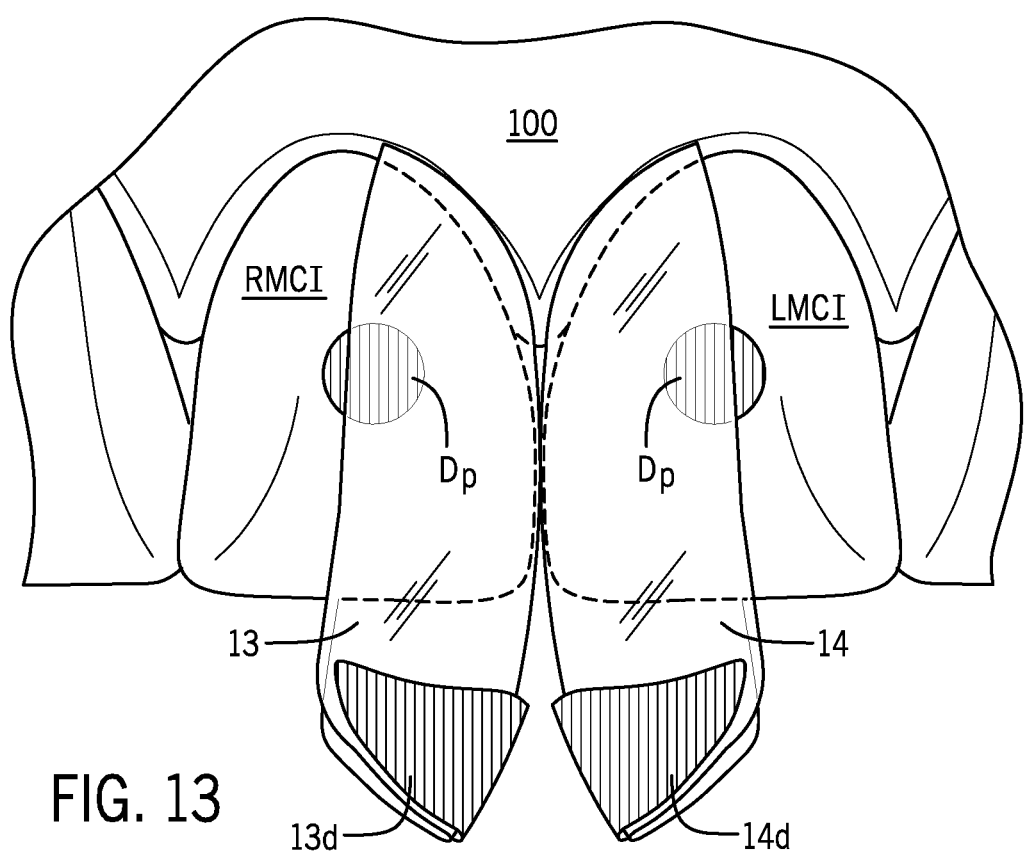
FIG. 13 shows a front view of a dental model illustrating a pair of color coded matrices of a first color inserted between maxillary central incisors.

FIGS. 11-13 show the use the graduated gauge 90 to select a pair of matrices to be used in a method for treating recessed gingival papilla having a black space of about 0.50 millimeters in width. However, the graduated gauge 90 can be used to select a pair of matrices to treat recessed gingival papilla having a black space of a different width.

Figure 14:
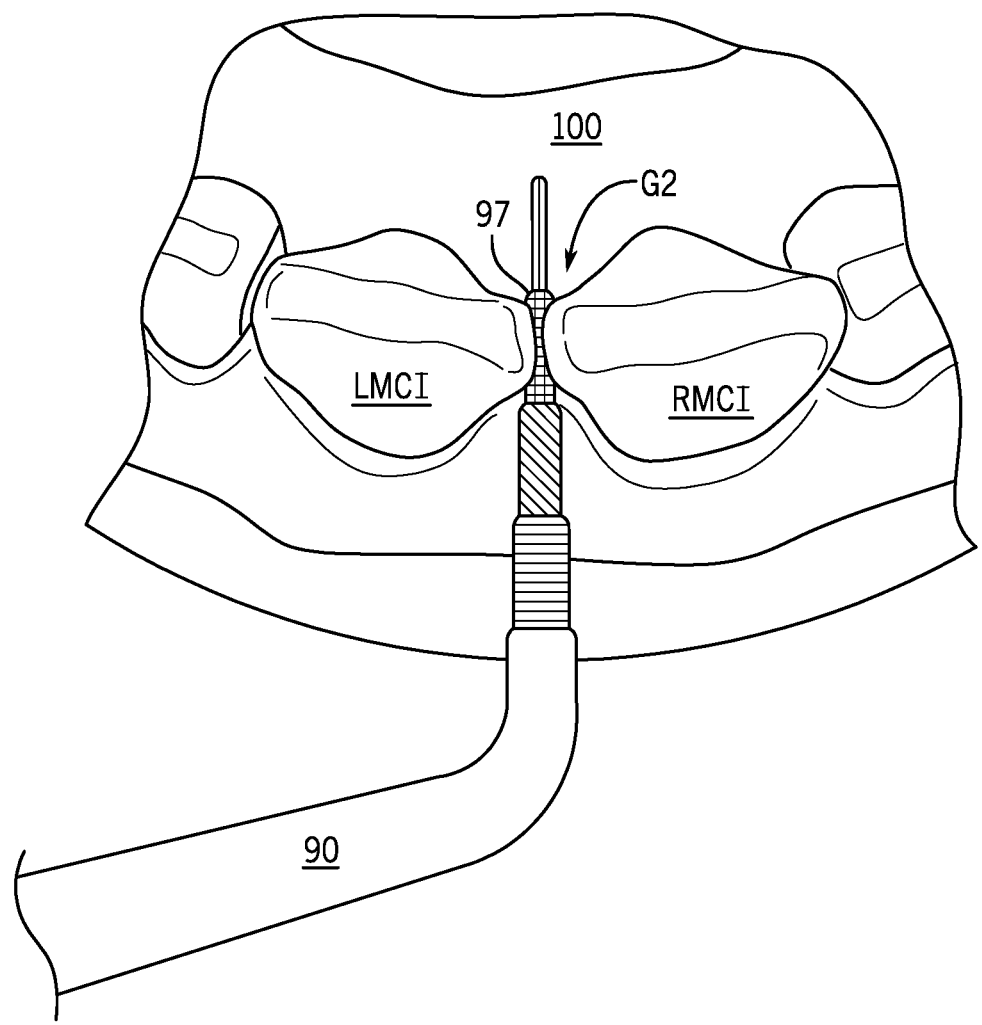
FIG. 14 shows a detailed view of the matrix selection tool of FIG. 9A inserted between maxillary central incisors of a dental model illustrating measurement of the width of a second diastema.
Figure 15:
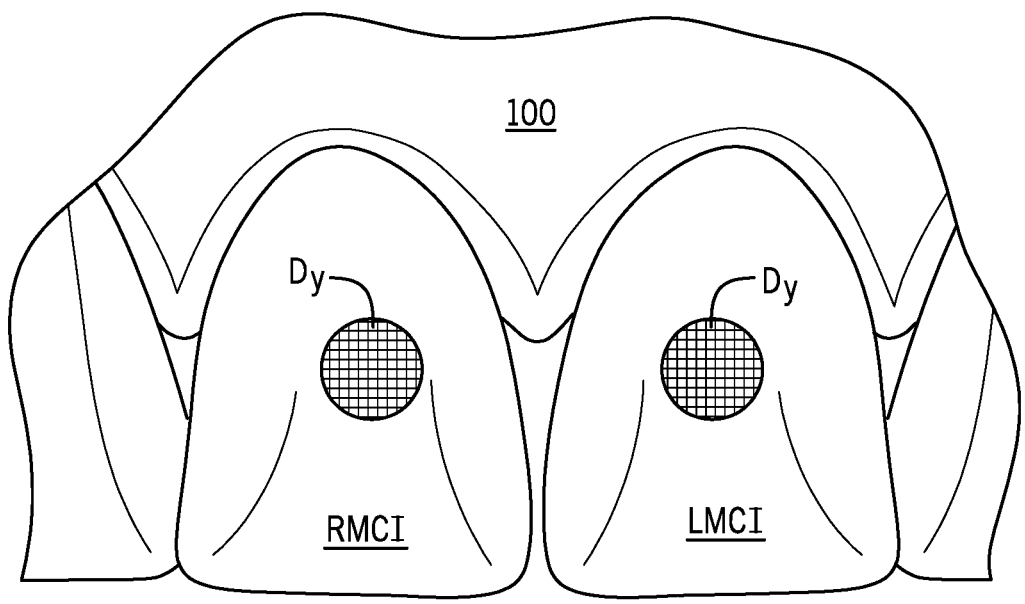
FIG. 15 shows a front view of a dental model illustrating color coding maxillary central incisors with a second color.
Figure 16:
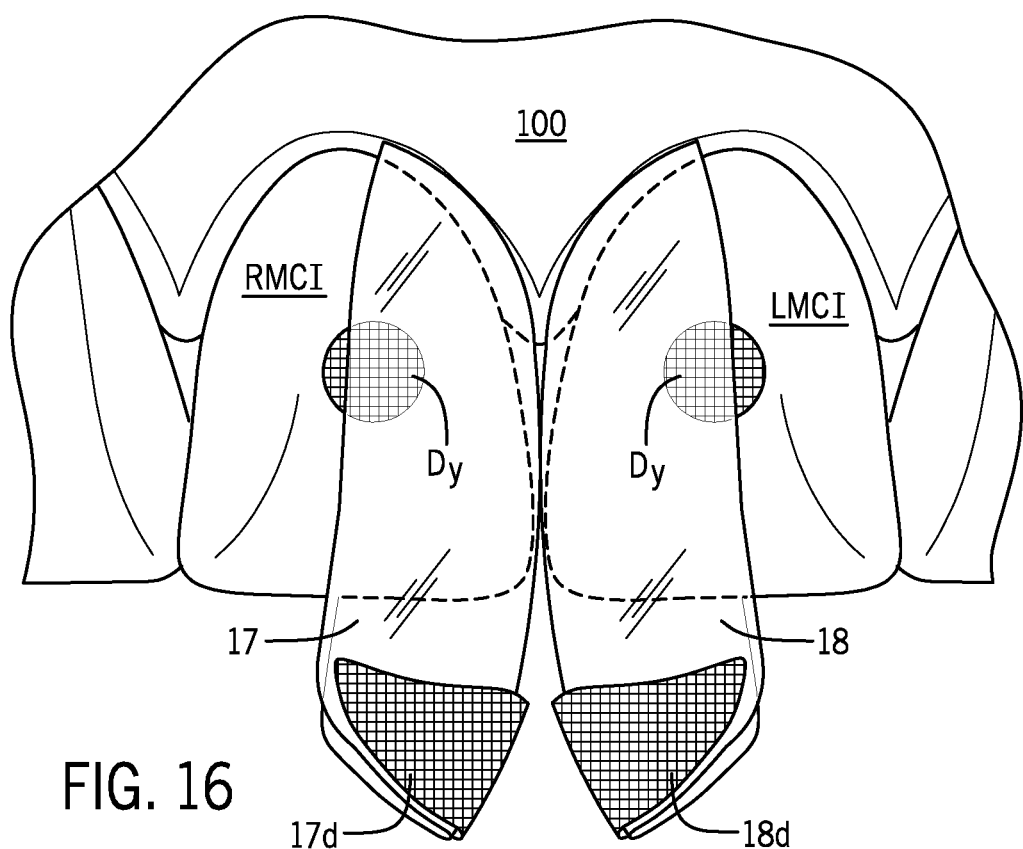
FIG. 16 shows a front view of a dental model illustrating a pair of color coded matrices of a second color inserted back to back between maxillary central incisors.

In FIG. 14, it can be seen that the third section 97 of the graduated gauge 90 (color coded yellow and having a 1 millimeter outside diameter) fits best in the gap G2 (modeling a space between teeth) between the right maxillary central incisor RMCI and the left maxillary central incisor LMCI of the dental model 100. This space can be referred to as a "yellow" sized space, and in FIG. 15, the right maxillary central incisor RMCI and the left maxillary central incisor LMCI are temporarily labeled with a yellow dye Dy indicating the space size. In FIG. 16, a pair of "yellow" sized matrices 17, 18 are placed in back to back relationship between the right maxillary central incisor RMCI and the left maxillary central incisor LMCI. Still looking at FIG. 16, the clear plastic anatomical sectional matrices 17, 18 can be placed around the maxillary central incisors and maintain anatomic root adaptation contact by way of an anatomic root end section of the matrices 17, 18. The matrices 17, 18 include yellow color coded sections 17d, 18d respectively. The right maxillary central incisor RMCI and the left maxillary central incisor LMCI can be restored using restorative materials as explained with reference to FIG. 13.

Figure 17:
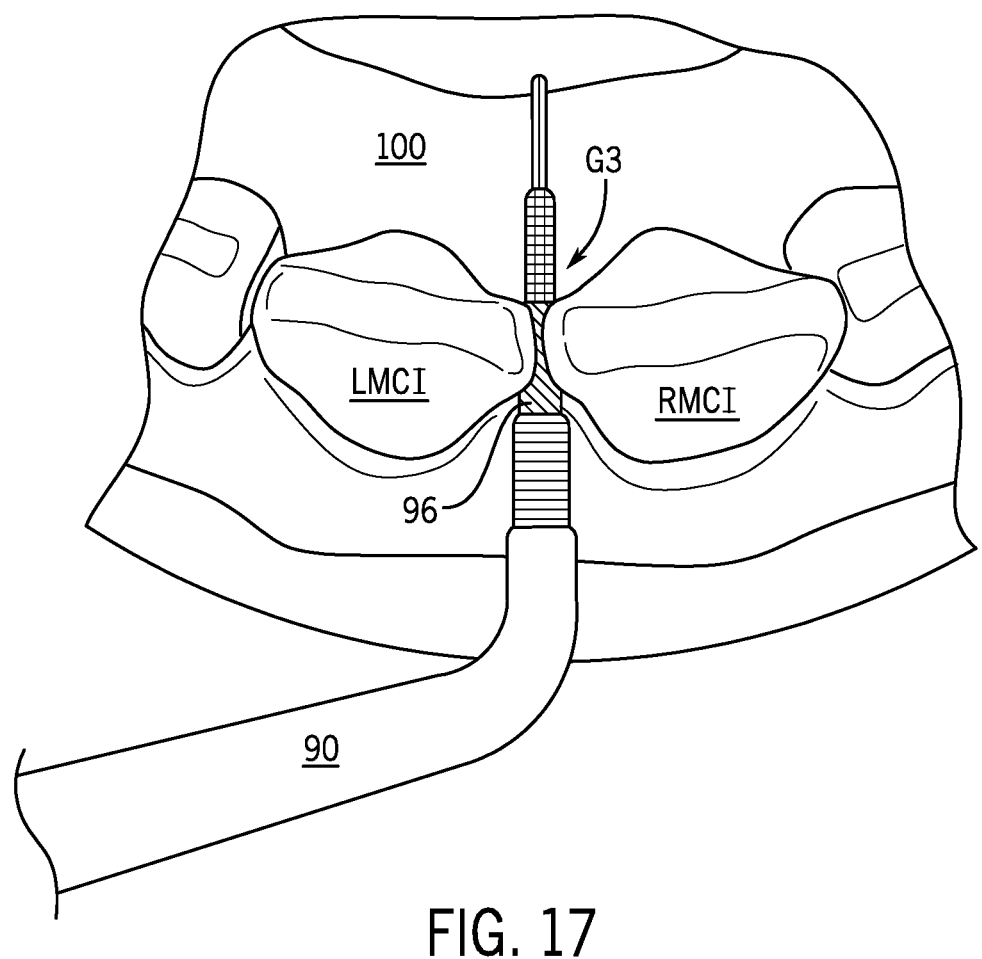
FIG. 17 shows a detailed view of the matrix selection tool of FIG. 9A inserted between maxillary central incisors of a dental model illustrating measurement of the width of a third diastema.
Figure 18:
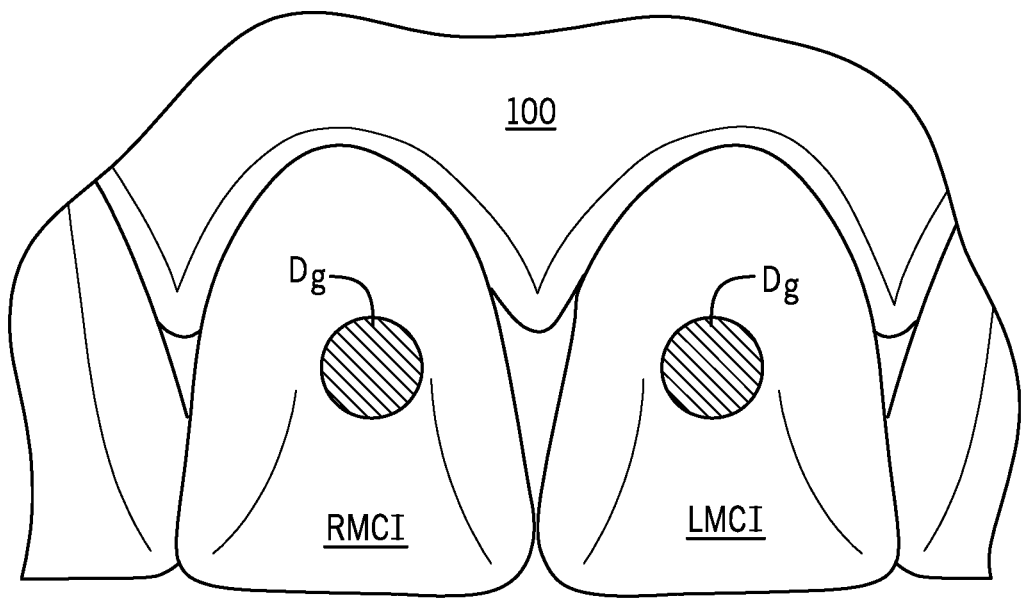
FIG. 18 shows a front view of a dental model illustrating color coding maxillary central incisors with a third color.
Figure 19:
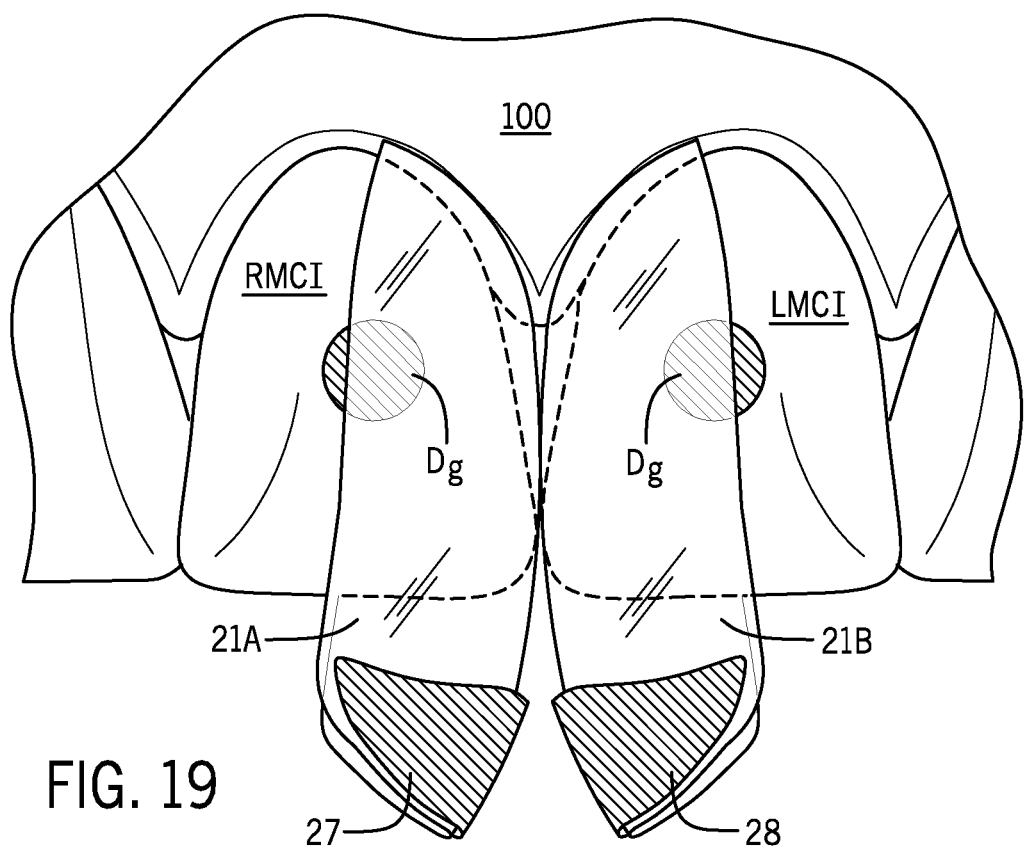
FIG. 19 shows a front view of a dental model illustrating a pair of color coded matrices of a third color inserted back to back between maxillary central incisors.

In FIG. 17, it can be seen that the second section 96 of the graduated gauge 90 (color coded green and having a 1.50 millimeter outside diameter) fits best in the gap G3 (modeling a space between teeth) between the right maxillary central incisor RMCI and the left maxillary central incisor LMCI of the dental model 100. This space can be referred to as a "green" sized space, and in FIG. 18, the right maxillary central incisor RMCI and the left maxillary central incisor LMCI are temporarily labeled with a green dye Dg indicating the space size. In FIG. 19, a pair of "green" sized matrices 21A, 21B are placed in back to back relationship between the maxillary central incisors. Still looking at FIG. 19, the clear plastic anatomical sectional matrices 21A, 21B can be placed around the right maxillary central incisor RMCI and the left maxillary central incisor LMCI and maintain anatomic root adaptation contact by way of an anatomic root end section of the matrices 21A, 21B. The matrices 21A, 21B include green color coded sections 27, 28 respectively. The maxillary central incisors can be restored using restorative materials as explained with reference to FIG. 13.

Figure 20:
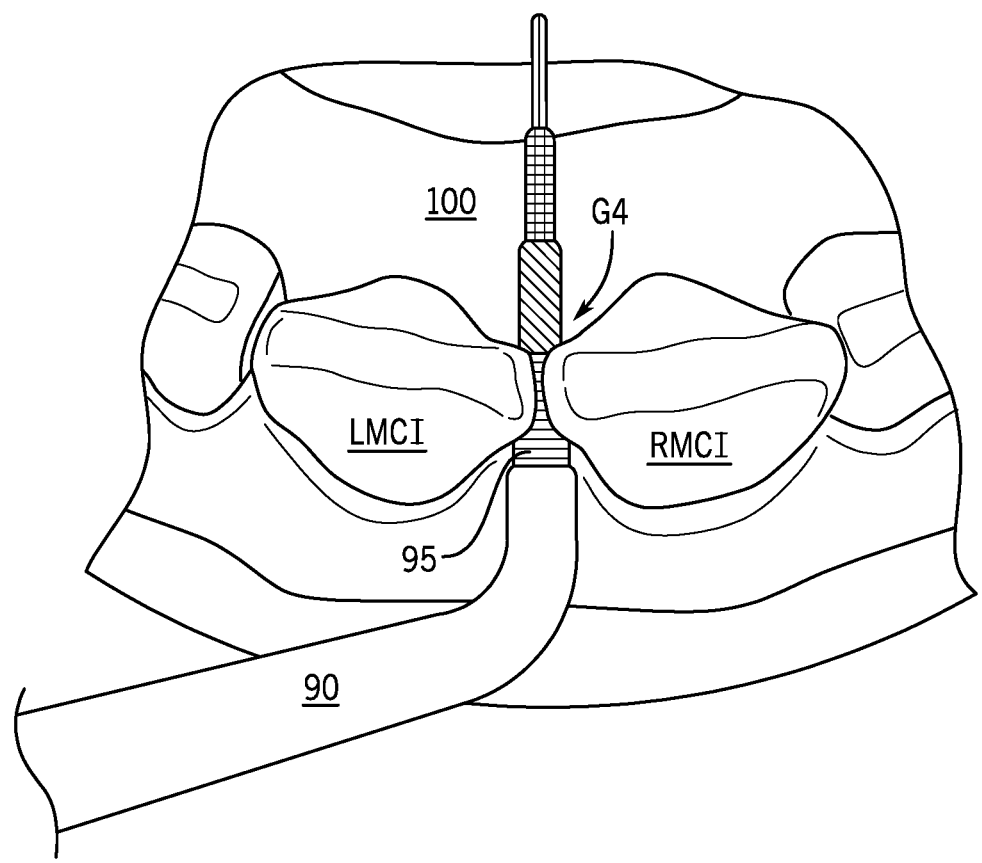
FIG. 20 shows a detailed view of the matrix selection tool of FIG. 9A inserted between maxillary central incisors of a dental model illustrating measurement of the width of a fourth diastema.
Figure 21:
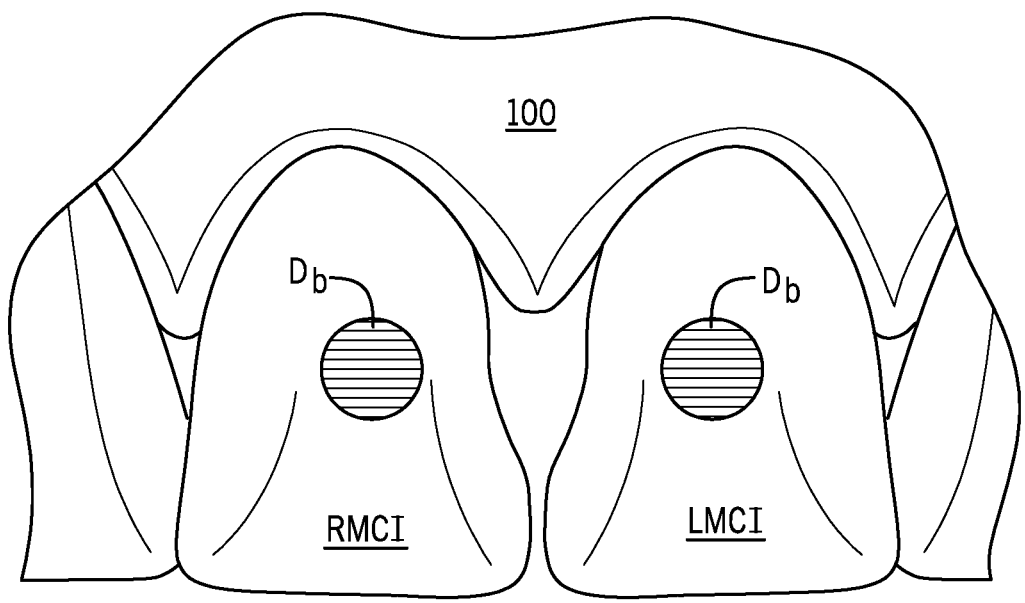
FIG. 21 shows a front view of a dental model illustrating color coding maxillary central incisors with a fourth color.
Figure 22:
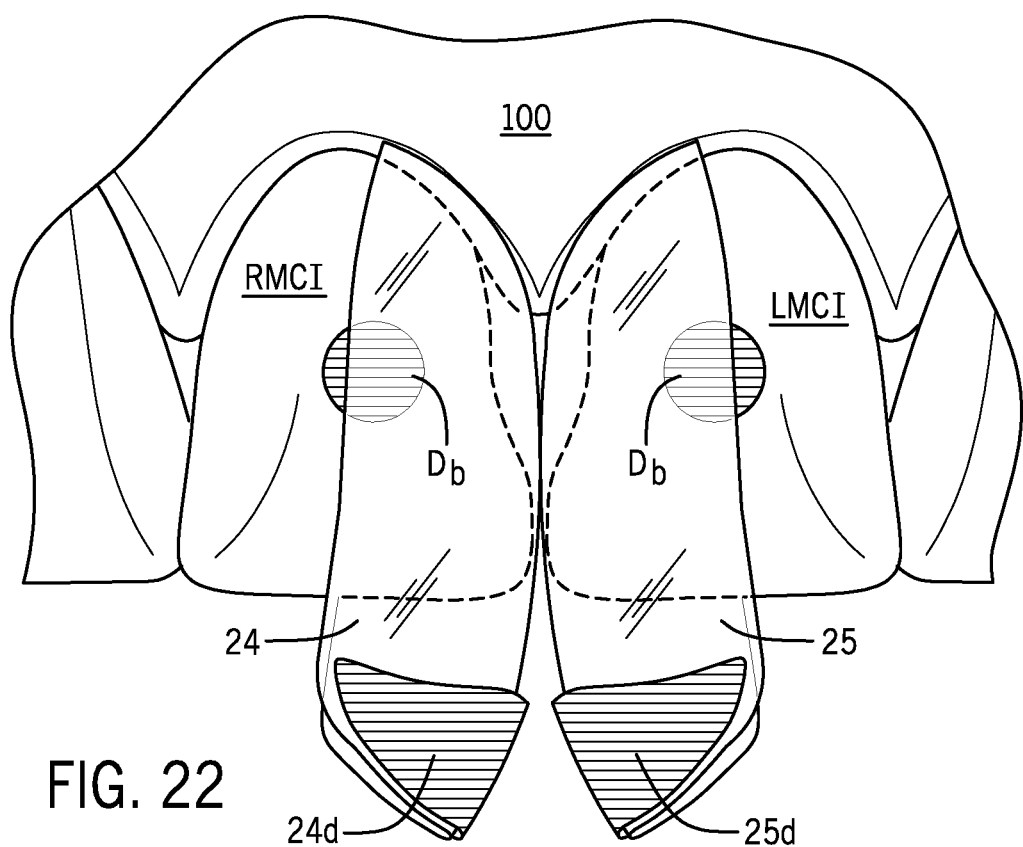
FIG. 22 shows a front view of a dental model illustrating a pair of color coded matrices of a fourth color inserted back to back between maxillary central incisors.

In FIG. 20, it can be seen that the first section 95 of the graduated gauge 90 (color coded blue and having a 2 millimeter outside diameter) fits best in the gap G4 (modeling a space between teeth) between the right maxillary central incisor RMCI and the left maxillary central incisor LMCI of the dental model 100. This diastema can be referred to as a "blue" sized space, and in FIG. 21, the right maxillary central incisor RMCI and the left maxillary central incisor LMCI are temporarily labeled with a blue dye Db indicating the space size. In FIG. 22, a pair of "blue" sized matrices 24, 25 are placed in back to back relationship between the right maxillary central incisor RMCI and the left maxillary central incisor LMCI. Still looking at FIG. 22, the clear plastic anatomical sectional matrices 24, 25 can be placed around the maxillary central incisors and maintain anatomic root adaptation contact by way of an anatomic root end section of the matrices 24, 25. The matrices 24, 25 include blue color coded sections 24d, 25d respectively. The maxillary central incisors can be restored using restorative materials as explained with reference to FIG. 13.

Thus, a method of the present disclosure to determine the actual clinical width of the black triangle that corresponds to the appropriate matrix utilizes a graduated gauge 90 that can be inserted between the teeth to record a measurement of the size (e.g., width in millimeters) of the black triangle. It should be appreciated that the use of the colors blue, green, yellow and pink in the sections 95, 96, 97, 98 of the graduated gauge 90 and the matrices 13, 14, 17, 18, 21A, 21B, 24 and 25 is a non-limiting example embodiment of the invention. Other colors can be used as indicia to match the size of the space to the pair of matrices. Alternatively, each surface section 95, 96, 97, 98 of the graduated gauge 90 can have a different indicia to be used as a gauge to select the matrices. The different indicia can be different numbers, or different symbols, for example. In addition, the graduated gauge 90 may have a different number of indicia coded sections to match a different number of indicia coded matrices. Also, alternative matrix selection tools can be used in place of the graduated gauge 90. For example, the width of the space can be measured using optical measuring devices. The width obtained using such an optical measuring device can be matched to a pair of matrices by looking at table correlating the measured width to a color of the proper pair of matrices. Furthermore, the graduated gauge 90 and the matrices 13, 14, 17, 18, 21A, 21B, 24 and 25 can be used between any neighboring teeth, not just the maxillary central incisors described in FIGS. 10 to 22.

A kit of the present invention may include a matrix selection tool (e.g., the graduated gauge 90) and a supply of a plurality of each of the indicia (e.g., color) coded matrices which may have different curvatures, from mild to aggressive that are designed to be sold in at least four degrees of curvature. The multiple matrices with differing amounts of gingival curve or bulge of the matrix accommodate different sizes of black triangles to treat different widths of black triangles, an enhancement in the contact area.

Figure 23A:
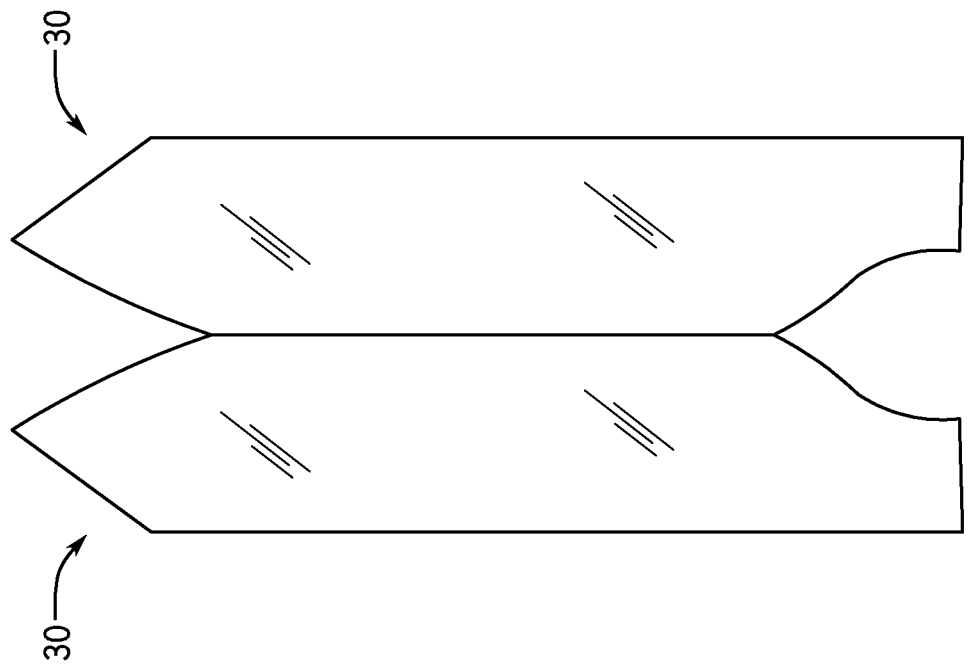
FIG. 23A is a front view of two of the matrices of FIG. 23 placed in back to back relationship.
Figure 23:
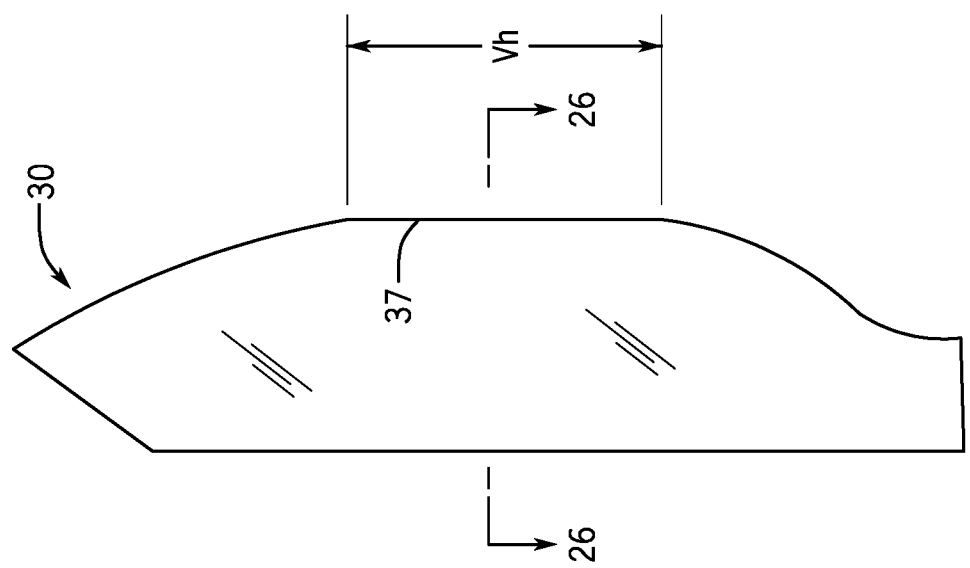
FIG. 23 is a front view of a dental matrix suitable for use in the method of the present disclosure.
Figure 25:
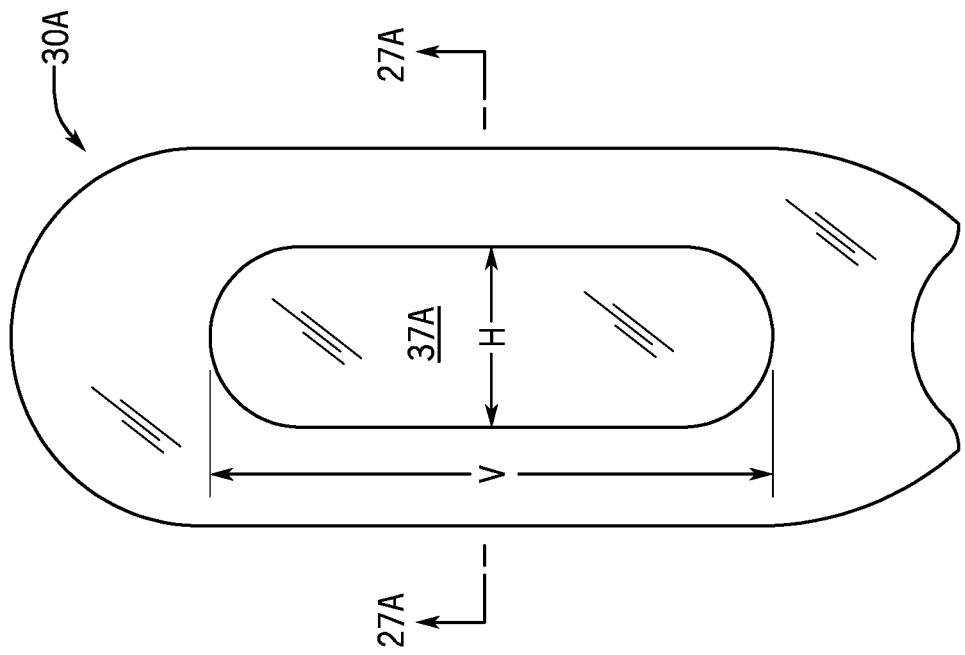
FIG. 25 is a side view of the matrix of FIG. 24.
Figure 26:
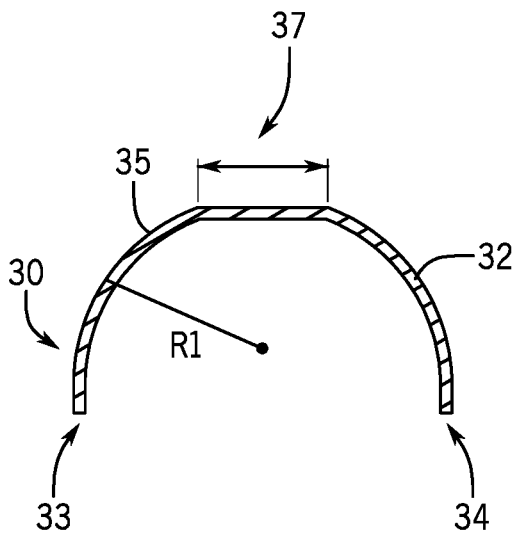
FIG. 26 is a cross sectional view of the dental matrix of FIG. 23 taken along line 26-26 of FIG. 23.

FIGS. 23, 24, 25, 26, 27A, 27B, 27C, 28A, and 28B show various advantageous features in a matrix that may be dimensioned and indicia (e.g., color) coded as in matrices 13, 14, 17, 18, 21A, 21B, 24 and 25. In FIGS. 23 and 26, there is shown one embodiment of a matrix 30 that may be dimensioned and color coded as in matrices 13, 14, 17, 18, 21A, 21B, 24 and 25. The matrix 30 has a curved strip 32 of translucent material (e.g., Mylar® polyester film). The strip 32 has a length from a first end 33 to a second end 34 sufficient to create a form for molding a restorative material to a surface of a tooth being restored. The strip 32 has a side surface 35 including a radius R1. The matrix 30 can be placed on the surface of a tooth (e.g., right maxillary central incisor) to pair with a second matrix 30 on the surface of an adjacent tooth (e.g., left maxillary central incisor) as shown in FIG. 23A with ideal tension when the correct curvatures happen to match the black triangle space. The matrix 30 has an interrupted radius area 37 which is flat and has a vertical height Vh of approximately 3.5 millimeters (see FIG. 23) and a horizontal width of approximately 1.5 millimeters (see FIG. 26). The interrupted radius area 37 is located at a contact area of the tooth being restored when the matrix is placed on the tooth being restored.

Figure 24:
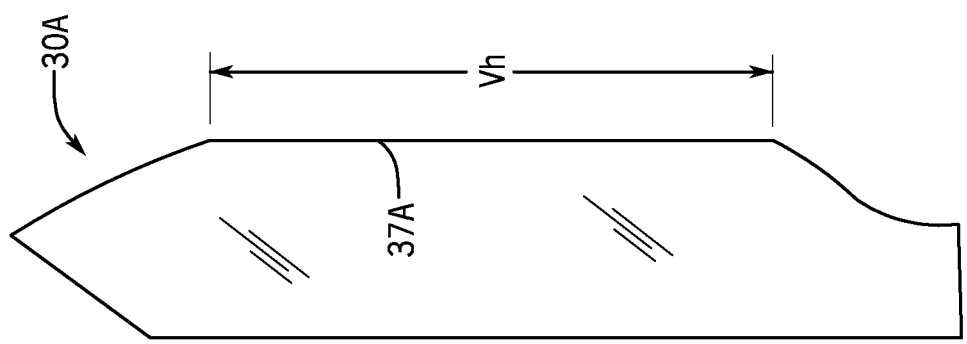
FIG. 24 is a front view of another dental matrix suitable for use in the method of the present disclosure.
Figure 27A:
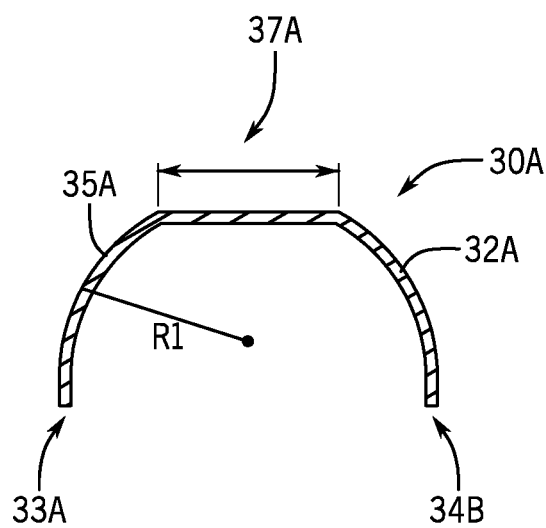
FIG. 27A is a cross-sectional view of the dental matrix of FIG. 25 taken along line 27A-27A of FIG. 25.

In FIGS. 24, 25 and 27A, there is shown another embodiment of a matrix 30A that may be dimensioned and color coded as in matrices 13, 14, 17, 18, 21A, 21B, 24 and 25. The matrix 30A has a curved strip 32A of translucent material (e.g., Mylar® polyester film). The strip 32A has a length from a first end 33A to a second end 34A sufficient to create a form for molding a restorative material to a surface of a tooth being restored. The strip 32A has a side surface 35A including a radius R1. The matrix 30A can be placed on the surface of a tooth (e.g., mesial surface of the right maxillary central incisor) to pair with a second matrix 30A on the surface of an adjacent tooth (e.g., mesial surface of the left maxillary central incisor) as shown in FIG. 23A with ideal tension when the correct curvatures happen to match the black triangle space. The matrix 30A has an interrupted radius area 37A which is flat. The matrix 30A has an interrupted radius area 37A which is flat and has a vertical height Vh of approximately 8 millimeters (see FIG. 24). The interrupted radius area 37A is located at a contact area of the tooth being restored when the matrix is placed on the tooth being restored.

Figure 27B:
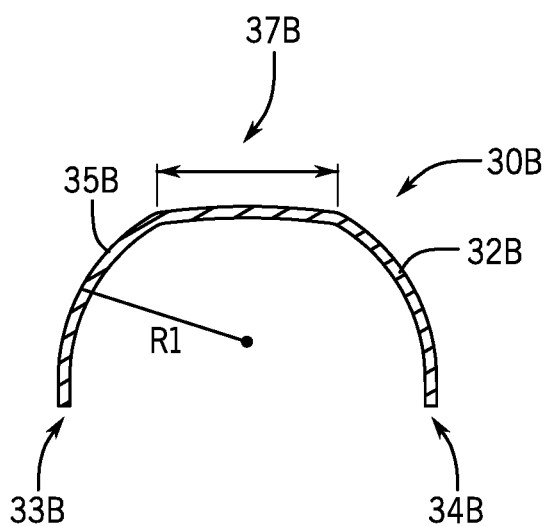
FIG. 27B is a cross-sectional view, similar to FIG. 27A, of another dental matrix suitable for use in the method of the present disclosure.

In FIG. 27B, there is shown another embodiment of a matrix 30B that may be dimensioned and color coded as in matrices 13, 14, 17, 18, 21A, 21B, 24 and 25. The matrix 30B has a curved strip 32B of translucent material (e.g., Mylar® polyester film). The strip 32B has a length from a first end 33B to a second end 34B sufficient to create a form for molding a restorative material to a surface of a tooth being restored. The strip 32B has a side surface 35B including a radius R1. The matrix 30B can be placed on the surface of a tooth (e.g., mesial surface of the right maxillary central incisor) to pair with a second matrix 30B on the surface of an adjacent tooth (e.g., mesial surface of the left maxillary central incisor) as shown in FIG. 23A with ideal tension when the correct curvatures happen to match the black triangle space. The matrix 30B has an interrupted radius area 37B which is flattened but retains slight curvature. The flattened area 37B can have a second radius of curvature that is larger than a first radius of curvature based on radius R1 of the section of the side surface 35B adjacent the flattened area 37B. The interrupted radius area 37B is located at a contact area of the tooth being restored when the matrix is placed on the tooth being restored.

Figure 27C:
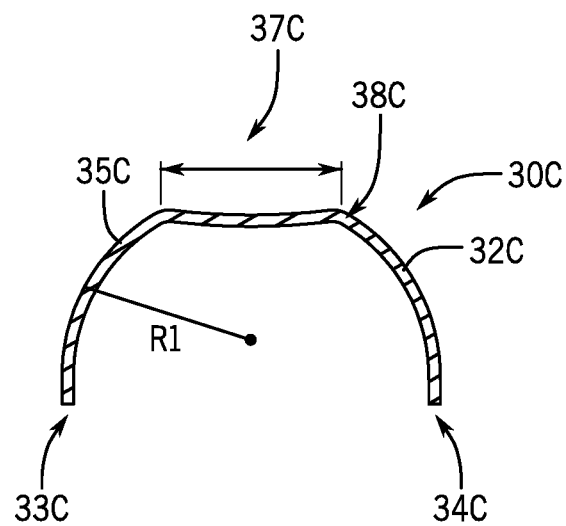
FIG. 27C is a cross-sectional view, similar to FIG. 27A, of another dental matrix suitable for use in the method of the present disclosure.

In FIG. 27C, there is shown another embodiment of a matrix 30C that may be dimensioned and color coded as in matrices 13, 14, 17, 18, 21A, 21B, 24 and 25. The matrix 30C has a curved strip 32C of translucent material (e.g., Mylar® polyester film). The strip 32C has a length from a first end 33C to a second end 34C sufficient to create a form for molding a restorative material to a surface of a tooth being restored. The strip 32C has a side surface 35C including a radius R1. The matrix 30C can be placed on the surface of a tooth (e.g., mesial surface of the right maxillary central incisor) to pair with a second matrix 30C on the surface of an adjacent tooth (e.g., mesial surface of the left maxillary central incisor) as shown in FIG. 23A with ideal tension when the correct curvatures happen to match the black triangle space. The matrix 30C has an interrupted radius area 37C which is concave in relation to the outer surface 38C. The interrupted radius area 37C is located at a contact area of the tooth being restored when the matrix is placed on the tooth being restored.

Thus, FIGS. 26, 27A, 27B, and 27C show views of different matrices 30, 30A, 30B, and 30C with a designated interrupted radius area (smaller flat=FIG. 26, larger flat=FIG. 27A, flattened with slight curvature=FIG. 27B, or concave area=FIG. 27C). The interrupted radius areas 37, 37A, 37B, 37C (flat, flat, flattened or concave area) may be approximately 4 millimeters (top to bottom direction V in FIG. 25) by 1.5 millimeters (front to back direction H in FIG. 25) in size but can be as great as 12 millimeters by 5 millimeters top to bottom direction V in size or as small as 1 millimeter by 0.25 millimeters front to back direction H from incisal to gingival, and is designed to mate with the same flat area of a second matrix in back to back relationship (e.g., as shown in FIG. 23A). The interrupted radius areas 37, 37A, 37B, 37C of one matrix pair nicely with the neighboring interrupted radius areas 37, 37A, 37B, 37C of another matrix when placed on adjacent teeth and the delicate polymeric film of the matrix resists the tendency to crumple or invert as shown in FIGS. 3-5.

As another advantage, the matrices 13, 14, 17, 18, 21A, 21B, 24 and 25 can be tooth specific. For example: maxillary central incisor, maxillary lateral incisor, maxillary canine, mandibular incisor, etc. Alternatively, the matrices 13, 14, 17, 18, 21A, 21B, 24 and 25 can simply go from small to large to accommodate different teeth with variations in size present in all human dentitions. There is also a wide range difference in sizes between different sized patients, such as small females to large males. A central incisor, for example can vary between 7 millimeters in width up to 11 millimeters in width. By "tooth specific", it is meant that at least a section of the matrix 13, 14, 17, 18, 21A, 21B, 24 and 25 is configured to conform to the shape of the outer surface of the specific natural tooth being restored, such as (without limitation) a maxillary lateral incisor.

As another advantage, the matrices 13, 14, 17, 18, 21A, 21B, 24 and 25 can be tooth type specific. By "tooth type specific" it is meant that at least a section of the matrix is configured to conform to the shape of the outer surface of the specific type of natural tooth such as (without limitation) an incisor.

As another advantage, the matrices 13, 14, 17, 18, 21A, 21B, 24 and 25 can be tooth surface specific. By "tooth surface specific" it is meant that at least a section of the matrix is configured to conform to the shape of the outer surface of the specific natural tooth surface such (without limitation) a lingual or buccal incisor surface.

Figure 28A:
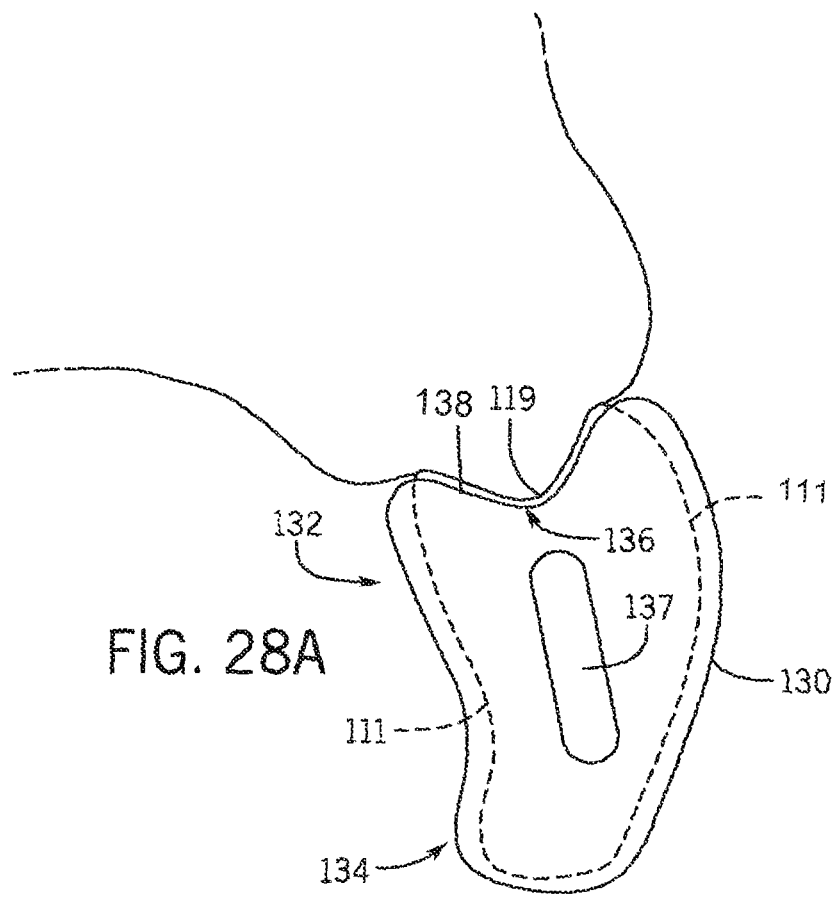
FIG. 28A shows a mesial view of another dental matrix, positioned on the human left central incisor, for use in the method of the present disclosure.

Referring now to FIG. 28A, a mesial view of another non-limiting example dental matrix 130 according to the invention is shown. In FIG. 28A, an upper incisor 111 having a clear sectional dental matrix 130 placed on the incisor 111 is shown. The dental matrix 130 can be formed from a translucent or transparent material such as a polymeric film. One non-limiting example material is the polyester film commercially available as Mylar™. The matrix 130 has a strip of material having a length from a first end to a second end sufficient to create a form for molding a restorative material to a surface of a tooth being restored. The length of the pre-curved matrix 130 is approximately 13 millimeters and the height can range approximately from 10 millimeters to 13 millimeters.

The matrix 130 has a root end section 132 that is anatomic in shape. The root end section 132 terminates at a gingival edge 138. The actual anatomic shapes of the root end section 132 of the matrix 130 can be created from scans of natural teeth, molds of natural teeth, and/or molds of tooth models. Thus, by "anatomic", it is meant that the root end section 132 of the matrix 130 has an inner surface that conforms to the shape of the outer surface of a particular region of the natural tooth that contacts the root end section 132 of the matrix 130.

The mesial side of the root end section 132 of the matrix 130 has an upward cut away 136 creating a gingival edge 138 that corresponds in shape to an upward projection of gingival papilla at the gingival margin 119 adjacent the tooth 111 and underlying periodontal and bony attachments of the tooth 111. The distal side of the root end section 132 of the matrix 130 can also have an upward cut away 136 creating a gingival edge 138 that corresponds in shape to an upward projection of gingival papilla at the gingival margin 119 adjacent the tooth 111 and underlying periodontal and bony attachments of the tooth 111. The root end section 132 of the matrix 130 can be fully or partially anatomic. As a result, the matrix 130 can be used without interdental wedges or elastic separators or spacers. The anatomic shape allows hands-free and wedge-free use as the matrix 130 hugs the tooth 111. The root end section 132 can have a vertical dimension in the range of 0.5 to 2 millimeters. The sectional matrix 130 has a second section 134 that is integral with the root end section 132. In the non-limiting embodiment of FIG. 28A, the second section 134 of the matrix 130 is anatomically shaped to conform to the shape of the outer surface of the tooth 111. The matrix 130 has an interrupted radius area 137 that may be formed in any of the configurations of interrupted radius areas 37, 37A, 37B, 37C of matrices 13, 14, 17, 18, 21A, 21B, 24 and 25. The matrix 130 may be indicia (e.g., color) coded as in matrices 13, 14, 17, 18, 21A, 21B, 24 and 25.

Figure 28B:
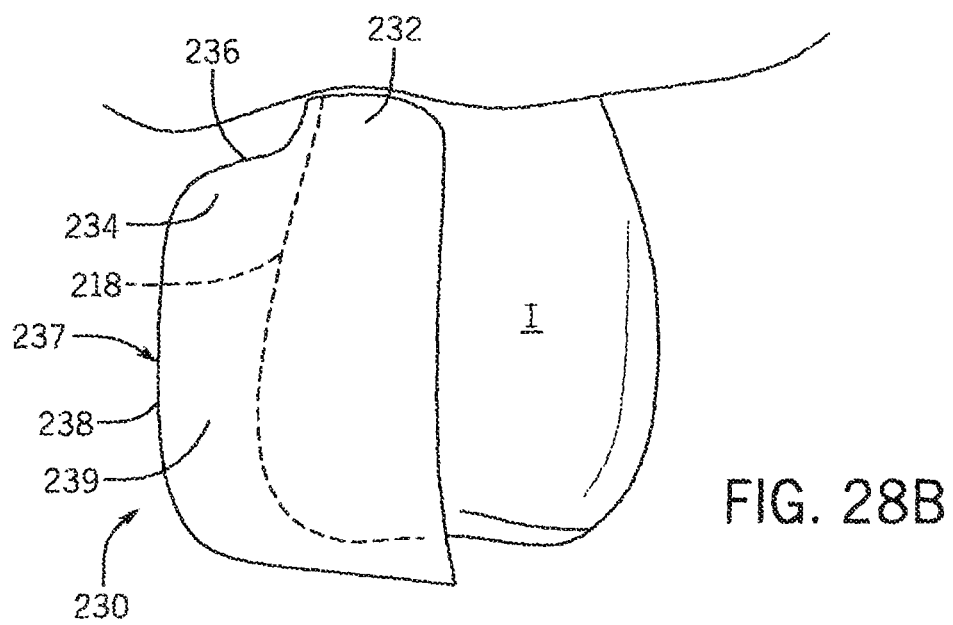
FIG. 28B is a front view of an incisor having another dental matrix for use in the method of the present disclosure.
Figure 29:
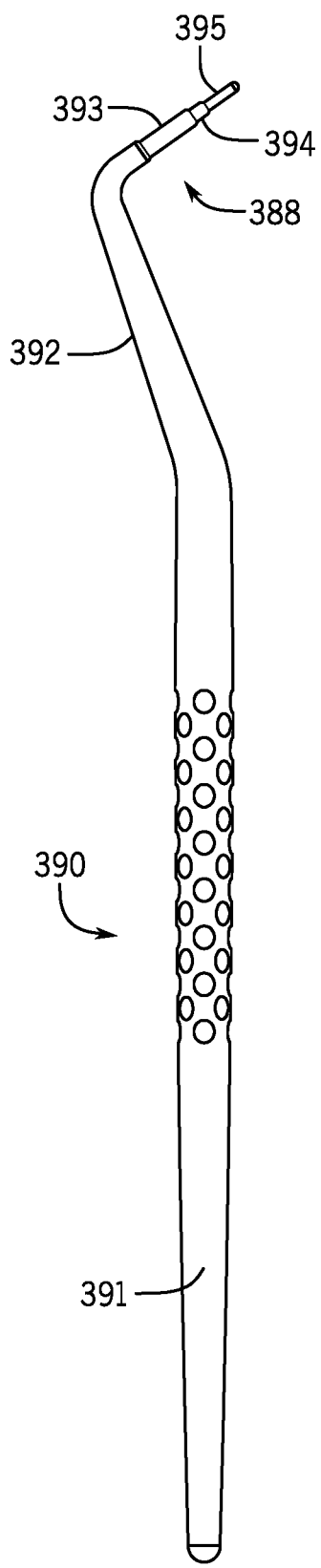
FIG. 29 is a side view of a depth of cure gauge of the present invention.
Figure 30:
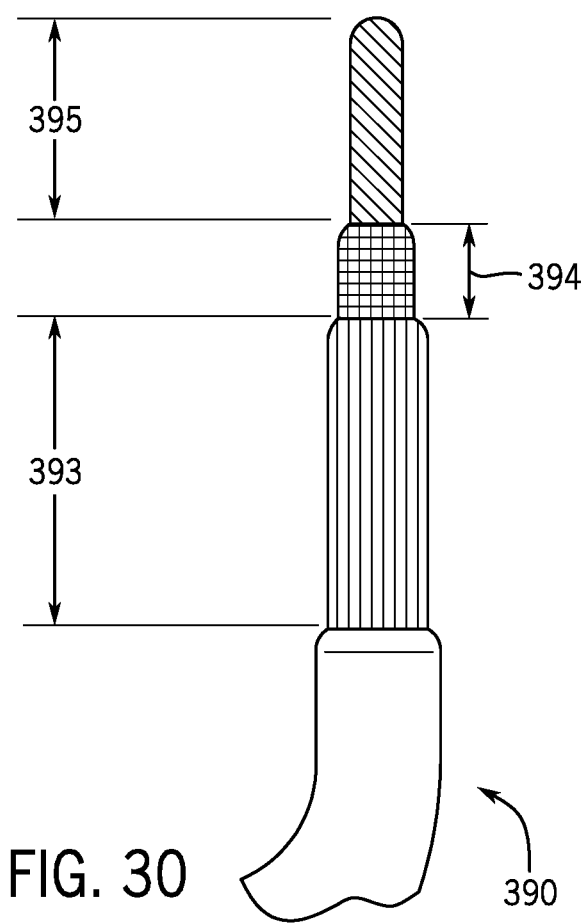
FIG. 30 is a detailed view of the distal end section of the depth of cure gauge of FIG. 29.
Figure 31:
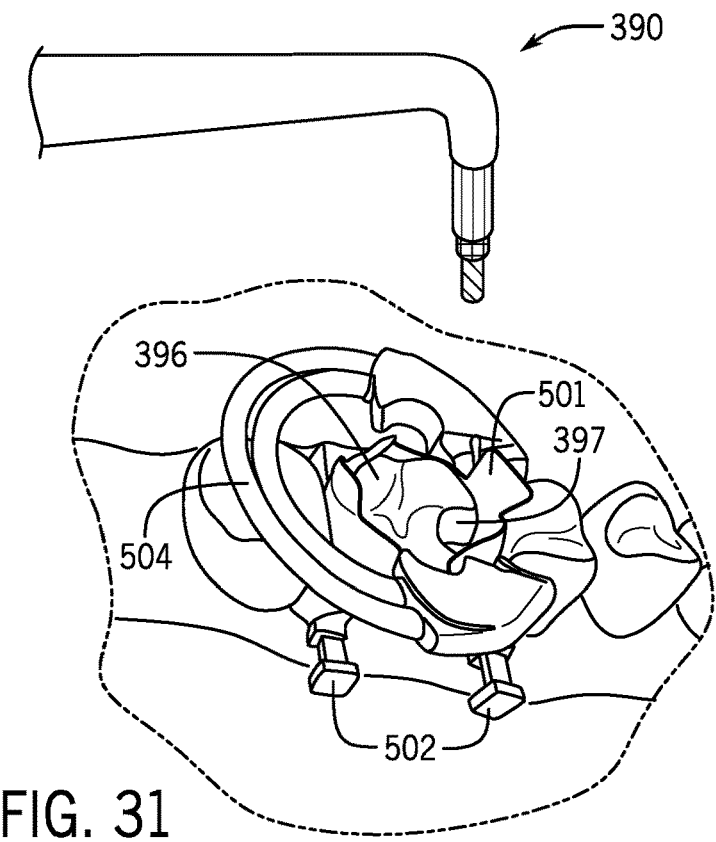
FIG. 31 is a perspective view of the depth of cure gauge of FIG. 29 before insertion in a hollow cavity preparation of a tooth.
Figure 32:
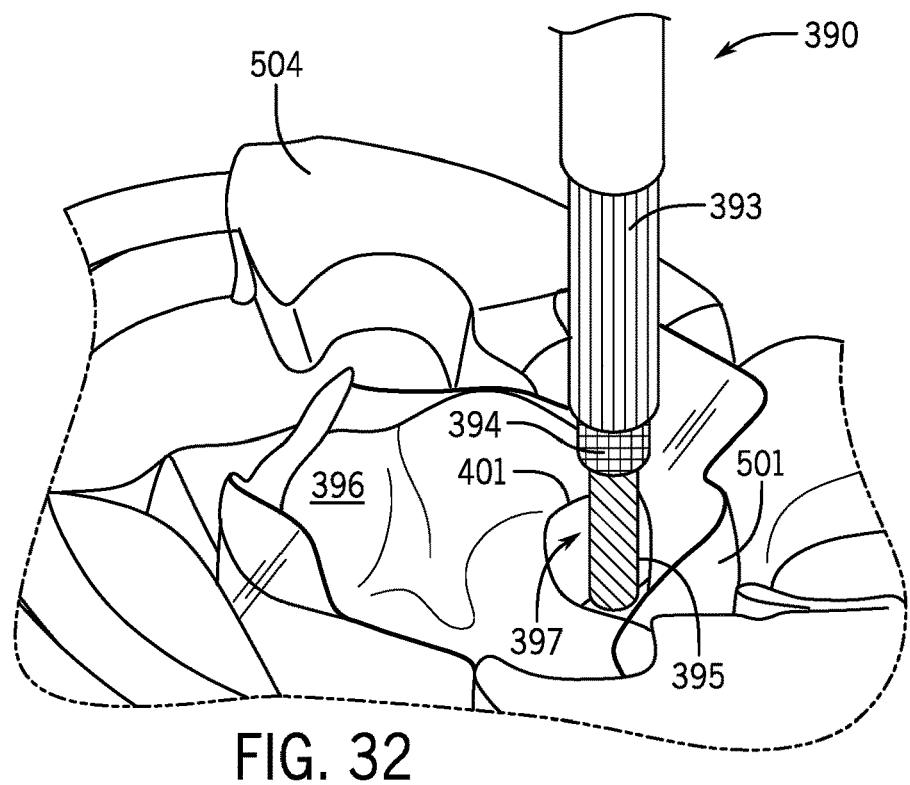
FIG. 32 is a detailed perspective view of the depth of cure gauge of FIG. 29 after insertion in the hollow cavity preparation of the tooth.

Turning now to FIG. 28B, a facial view of another non-limiting example dental matrix 230 according to the invention is shown on an incisor I. The dental matrix 230 can be formed from a translucent or transparent material such as a polymeric film. One non-limiting example material is the polyester film commercially available as Mylar™. The matrix 230 has a first root end section 232 that is anatomic in shape. The actual anatomic shapes of the root end section 232 of the matrix 230 can be created from scans of natural teeth, molds of natural teeth, and/or molds of tooth models. Thus, by "anatomic", it is meant that the root end section 232 of the matrix 230 has an inner surface that conforms to the shape of the outer surface of a particular region of the natural tooth that contacts the root end section 232 of the matrix 230. In FIG. 28B, the root end section 232 of the matrix 230 conforms to the outer surface of the gingival portion of the incisor I. The root end section 232 of the matrix 230 can be fully or partially anatomic. As a result, the matrix 230 can be used without interdental wedges or elastic separators or spacers. The anatomic shape allows hands-free and wedge-free use as the matrix 230 hugs the incisor I.

The sectional matrix 230 has a second (crown root junction profile) section 234 that is integral with the root end section 232. The second section 234 is not anatomically shaped to conform to the shape of the outer surface 218 of the incisor I. The outer surface 218 may have been created by removal of portions of the incisor I. Specifically, looking at FIG. 28B, an exaggerated root-crown profile 236 of the second section 234 is created at the junction of the root end section 232 and the second section 234. The exaggerated root-crown profile 236 extends away from the outer surface 218 of the incisor I. The exaggerated root-crown profile 236 merges with a side profile 238 of the second section 234 of the matrix 230. The exaggerated root-crown profile 236 and the side profile 238 of the second section 234 of the matrix 230 create a mild to severe non-anatomic bulge. The space 239 between the outer surface 218 of the incisor I and the inner surface of the exaggerated root-crown profile 236 and the side profile 238 creates a mold for the dental filling material that closes a diastema between teeth. The matrix 230 has an interrupted radius area 237 that may be formed in any of the configurations of interrupted radius areas 37, 37A, 37B, 37C of matrices 13, 14, 17, 18, 21A, 21B, 24 and 25. The matrix 230 may be indicia (e.g., color) coded as in matrices 13, 14, 17, 18, 21A, 21B, 24 and 25.

Because gingiva adapts to a wide range of shapes, clinicians can now create convenient interproximal shapes using a pair of complementary matrices 13, 14, 17, 18, 21A, 21B, 24, 25, 130 and 230 where the restorations are smooth and without a sharp marginal ledge. Bridge abutments and exotic implant emergence profiles have aptly demonstrated this clinical reality. Restoratively driven papilla regeneration according to the invention should become a viable option for all restorative dentists. Until now, there were very few dedicated tools or techniques for restoratively driven papilla regeneration. Previous attempts at both diastema closure and papilla regeneration using direct composites often ended with significant compromise in periodontal health. The interdental papilla serves as both an esthetic and functional asset, and anatomically ideal interproximal composite shapes formed using the methods of the invention can serve as a predictable scaffold to regain this valuable gingival architecture.

It is becoming increasingly common for dentists to take digital impressions of teeth after grinding a tooth down for purposes of rebuilding the tooth with materials like zirconia, porcelain, gold, etc. The crown or veneer is then milled with CAD CAM and then cemented onto the stump of residual tooth. Sometimes the tooth is scanned before the grinding of the tooth to obtain a form that will be duplicated in the milled restoration.

The grinding of the tooth is traumatic and more conservative treatments are needed. Currently, matrices sold under the trademark Bioclear® provide a myriad of prefabricated shapes but a customized matrix specific for every tooth in every patient would be beneficial.

To meet this need, the present invention also provides a method for using a gauge, a digital scanner, an x-ray device, an ultrasonic device, an MRI imaging device, or another imaging device to record the shape of a tooth digitally. Then designs are made digitally to restore a broken, diseased or worn tooth or to add to a tooth for cosmetic or functional reasons, and then a matrix or a set of matrices are printed or milled either chairside or remotely, to then be placed on or around the tooth to allow injection molding and injection over-molding of said tooth.

When used in dental restoration techniques, light curable composite resins require light in a certain wavelength to excite a photo-initiator, which begins the polymerization process. If the light penetration is insufficient, poor initiation of this reaction can result, which can lead to under-cured or uncured material. The incomplete curing of composite resins is associated with a reduction in their mechanical properties and biocompatibility. As a result, manufacturers and suppliers of dental resins provide recommendations about depth of cure. For example, a manufacturer may recommend the use of some specific light exposure time to cure a two millimeter or four millimeter thickness of composite resin. Accordingly, dentists place light curable flowable composite resins in increments, such as two or four millimeters, to achieve good depth of cure.

With deeper cavity preparations, it can be appreciated that it takes time to place, adapt and cure each increment of a plurality of increments. However, reduction in the number of increments is limited by manufacturer's recommendations on a maximum thickness of composite resin that provides an acceptable depth of cure. Therefore, what is needed is a device that allows a dentist to determine the depth of a cavity preparation so that manufacturer's recommendations on a maximum thickness of composite resin for adequate depth of cure are not exceeded.

The foregoing need is satisfied by a measuring gauge comprising: a handle section; and a distal end section connected to the handle section. The distal end section includes a plurality of contiguous surface sections. Each surface section has a different indicia to be used as a gauge to select an appropriate thickness of light curable flowable composite resin to be placed in a cavity preparation. The different indicia can be different colors, or different numbers, or different symbols.

In a method of the present disclosure, a tooth can be restored using the steps of: (a) removing a portion of the tooth to form a hollow cavity preparation; (b) inserting the distal end section of the gauge into the hollow cavity preparation until a tip of the distal end section of the gauge contacts a bottom surface of the cavity preparation; (c) observing a location of an upper edge of the cavity preparation relative to the distal end section of the gauge and choosing one of the surface sections that is closest to the upper edge of the cavity preparation; (d) injecting a depth of light-curable flowable composite resin into the cavity preparation based on the indicia of the one of the surface sections that is closest to the upper edge of the cavity preparation; and (e) light curing the flowable composite contained in the cavity preparation.

Turning now to FIGS. 29-32, there is shown an example measuring gauge 390 of the invention suitable for assuring that the thickness of a layer of light curable flowable composite resin placed in the cavity preparation does not exceed recommendations on a maximum thickness of composite resin for adequate depth of cure. The tools and techniques for removing a portion of the top surface of the tooth and a portion of the interproximal surface of the tooth 396 to form the hollow cavity preparation 397 are well known in the art and therefore will not be explained further. A matrix 501, dental wedges 502 (such as those described in WO/2015/187927), and a separator ring 504 (such as that described in WO/2016/183360) are used in the tooth restoration depicted in FIGS. 31 and 32.

The measuring gauge 390 has a handle section 391, an intermediate section 392 angled 70° with respect to the handle section 391, and a distal end section 388 angled 105° with respect to the intermediate section 392. The distal end section 388 includes a first section 393 color coded red, a second section 394 color coded yellow, and a third section 395 color coded green.

The distal end section 388 of the measuring gauge 390 is inserted into a hollow cavity preparation 397 of a tooth 396 until a tip of the distal end section of the measuring gauge 390 contacts a bottom surface of the cavity preparation 397. See FIGS. 31 and 32. The dentist observes a location of an upper edge 401 of the cavity preparation 397 relative to the distal end section 388 of the measuring gauge 390 and chooses one of the surface sections 393, 394, 395 that is closest to the upper edge 401 of the cavity preparation 397. The color of the closest surface section is noted. For example, if the third section 395 (color coded green) is closest to the upper edge 401 of the cavity preparation 397, a situation referred to as "go" is presented in which the light curable flowable composite resin can be filled up to the upper edge 401 of the cavity preparation 397 and adequate depth of cure can be achieved. If the second section 394 (color coded yellow) is closest to the upper edge 401 of the cavity preparation 397, a situation referred to as "caution" is presented in which the light curable flowable composite resin can be filled up to the upper edge 401 of the cavity preparation 397 and adequate depth of cure can be achieved. However, caution is advised such that overfill of the light curable flowable composite resin does not occur. If the first section 393 (color coded red) is closest to the upper edge 401 of the cavity preparation 397, a situation referred to as "no go" is presented in which the light curable flowable composite resin cannot be filled up to the upper edge 401 of the cavity preparation 397. Two or more incremental layers of the light curable flowable composite resin must be used to assure adequate depth of cure for each layer.

The third section 395 (color coded green—"go") may have length of four millimeters from the tip of the distal end section of the measuring gauge 390. The second section 394 (color coded yellow—"caution") may be located from four to five millimeters from the tip of the distal end section of the measuring gauge 390. The first section 393 (color coded red—"no go") may be located starting at greater than five millimeters from the tip of the distal end section of the measuring gauge 390. Thus, the non-limiting example measuring gauge 390 is a 4 millimeter (green), 5 millimeter (yellow), and a no go (red) depth gauge as current bulk fill dental composites may have a 4 millimeter and 5 millimeter maximum depth of cure (e.g., interproximal is 5 millimeters, middle of the tooth is only 4 millimeters because of no 3-point curing, i.e., 3-point curing is from occlusal, buccal and lingual which is only possible in the interproximal).

Different manufacturers may have different recommendations on a maximum thickness of a specific composite resin that provides an acceptable depth of cure for the specific composite resin. Therefore, the measuring gauge 390 can be dimensioned specifically for a specific composite resin. For example, one composite resin may have a three millimeter depth of cure specification. A unique measuring gauge could be sold with this composite resin. The measuring gauge can have a second section (color coded green—"go") with a length of three millimeters from the tip of the distal end section of the measuring gauge. The measuring gauge can have a first section (color coded red—"no go") having a location starting at greater than three millimeters from the tip of the distal end section of the measuring gauge. Another composite resin may have a two millimeter depth of cure specification. A unique measuring gauge could be sold with this composite resin. The measuring gauge can have a second section (color coded green—"go") with a length of two millimeters from the tip of the distal end section of the measuring gauge. The measuring gauge can have a first section (color coded red—"no go") having a location starting at greater than two millimeters from the tip of the distal end section of the measuring gauge. Similar unique measuring gauges can be provided for composite resins having a different depth of cure.

Different manufacturers may have different recommendations on a maximum thickness of a specific composite resin that provides an acceptable depth of cure for the specific composite resin for specific tooth locations. For example, the maximum thickness of a specific composite resin that provides an acceptable depth of cure at an interproximal region of the tooth may be 5 millimeters, whereas an acceptable depth of cure for the same resin at a middle region of the tooth may be 4 millimeters. Therefore, the measuring gauge 390 can be dimensioned specifically for the specific composite resin, and the unique measuring gauge can be sold with this composite resin. A third section 395 of the measuring gauge 390 (color coded green—"go") may have length of four millimeters from the tip of the distal end section of the measuring gauge 390 indicating that the resin is suitable for filling all tooth locations. The second section 394 (color coded yellow—"caution") may have a location at four to five millimeters from the tip of the distal end section of the measuring gauge 390 indicating that the resin is suitable for filling interproximal tooth locations. The first section 393 (color coded red—"no go") may have a location of greater than five millimeters from the tip of the distal end section of the measuring gauge 390 indicating that the resin is not suitable for single layer curing.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A kit comprising:
   (i) a measuring gauge comprising:
      a handle section; and
      a distal end section connected to the handle section, the distal end section including graduated sections with different widths, wherein the gauge includes a different indicia associated with each of the widths; and
   (ii) a plurality of dental matrices, each of the dental matrices comprising a curved strip of material, the strip having a length from a first end to a second end sufficient to create a form for molding a restorative material to a surface of a tooth being restored,
   wherein a first of the dental matrices has a first matrix indicia corresponding to one of the different indicia of the gauge,
   wherein a second of the dental matrices has a second matrix indicia corresponding to another of the different indicia of the gauge,
   wherein the distal end section of the measuring gauge is configured to be inserted into a gap between adjacent teeth that includes the tooth being restored,
   wherein as the distal end section is inserted into the gap, a graduated section of the graduated sections is configured to fit best within the gap,
   wherein the indicia associated with the width of the graduated section corresponds to the first matrix indicia, such that the first of the dental matrices is selected over the second of the dental matrices to be placed on the tooth being restored,
   wherein the first of the plurality of dental matrices is a first dental matrix, the first dental matrix including a first section that includes the first matrix indicia, the first section is configured to be positioned past a biting surface of the tooth in a direction from a gingival end to the biting surface of the tooth when the first dental matrix is placed on the tooth; and
   wherein the second of the plurality of dental matrices is a second dental matrix, the second dental matrix including a second section that includes the second matrix indicia, the second section is configured to be positioned past the biting surface of the tooth in the direction from the gingival end to the biting surface of the tooth when the second dental matrix is placed on the tooth.

2. The kit of claim 1 wherein:
   the first of the dental matrices is a first dental matrix that includes a first radius and a first interruption in the first radius that is a first flattened area in a first intermediate section of the first dental matrix located at a first contact area of the tooth being restored when the first dental matrix is placed on the tooth being restored.

3. The kit of claim 2 wherein:
   the second of the dental matrices is a second dental matrix that includes a second radius and a second interruption in the second radius that is a second flattened area in a second intermediate section of the second dental matrix located at a second contact area of the tooth being restored when the second matrix is placed on the tooth being restored.

4. The kit of claim 3 wherein:
   the first flattened area of the first dental matrix has a radius of curvature that is larger than a radius of curvature of the first radius.

5. The kit of claim 1 wherein:
   the first of the dental matrices is a first dental matrix that includes a first radius and a first interruption in the first radius, the first interruption is a concave area in a first intermediate section of the first dental matrix, the first intermediate section located at a contact area of the tooth being restored when the first dental matrix is placed on the tooth being restored.

6. The kit of claim 1 wherein:
   the first matrix indicia is a first color and the second matrix indicia is a second color.

7. The kit of claim 1 wherein:
   the first matrix indicia is a first number and the second matrix indicia is a second number.

8. The kit of claim 1 wherein:
   the first matrix indicia is a first letter and the second matrix indicia is a second letter.

9. The kit of claim 1 wherein:
   the first of the dental matrices includes a convex inner surface at a root crown junction that extends into a second section thereby forming a bulge for positioning adjacent a gum line of the tooth being restored for closure of a space between the tooth being restored and an adjacent tooth, and
   the second of the dental matrices includes a convex inner surface at a root crown junction that extends into a second section thereby forming a bulge for positioning adjacent a gum line of the tooth being restored for closure of a space between the tooth being restored and an adjacent tooth,
   wherein the bulge of the first of the dental matrices and the bulge of the second of the dental matrices have different sizes.

10. The kit of claim 1, wherein the first of the plurality of dental matrices has a first curvature;
   wherein the second of the plurality of dental matrices has a second curvature; and
   wherein the first curvature is different than the second curvature.

11. The kit of claim 1, wherein the tooth is an anterior tooth.

12. The kit of claim 1, wherein the width of the graduated section is 1.5 millimeters, 2 millimeters, 2.5 millimeters, 3 millimeters, 4 millimeters, or 5 millimeters.

13. The kit of claim 1, wherein the graduated sections include:
   a first graduated section having a width of 1 millimeter; and
   a second graduated section adjacent the first graduated section, the second graduated section have a width of 1.5 millimeters.

14. The kit of claim 13, wherein the graduated sections include:

a third graduated section adjacent the second graduated section, the third graduated section having a width of 2 millimeters; and a fourth graduated section adjacent the third graduated section, the fourth graduated section having a width of 2.5 millimeters.

15. A kit comprising:

a measuring gauge comprising:
- a handle section; and
- a distal end section connected to the handle section, the distal end section including:
  - a first section having a first width and a first gauge indicia;
  - a second section having a second width different from the first width, and a second gauge indicia different than the first gauge indicia;

a plurality of dental matrices, each of the dental matrices comprising a curved strip of material, the strip having a length from a first end to a second end sufficient to create a form for molding a restorative material to a surface of a tooth being restored;

wherein a first of the dental matrices has a first matrix indicia corresponding to the first indicia of the gauge, the first of the dental matrices has a first section that includes the first matrix indicia, the first section configured to be positioned past a biting surface of a first tooth in a direction from a gingival end to the biting surface of the first tooth when the first of the dental matrices is placed on the first tooth;

wherein a second of the dental matrices has a second matrix indicia corresponding to the first indicia of the gauge, the second of the dental matrices has a second section that includes the second matrix indicia, the second section configured to be positioned past a biting surface of a second tooth in a direction from a gingival end to the biting surface of the second tooth when the second of the dental matrices is placed on the second tooth.

16. A kit comprising:

a measuring gauge comprising:
- a handle section; and
- a distal end section connected to the handle section, the distal end section including:
  - a first section having a first width and a first gauge indicia; and
  - a second section having a second width different from the first width and a second gauge indicia; and a first dental matrix having a first matrix indicia, the first dental matrix comprising a curved strip of material, the strip having a length from a first end to a second end sufficient to create a form for molding a restorative material to a surface of a tooth being restored;

wherein the distal end section of the measuring gauge is configured to be inserted into a gap between adjacent teeth;

wherein as the distal end section is inserted into the gap, the first section is configured to fit best within the gap;

wherein the first section fitting best within the gap facilitates the selection of the first dental matrix having the first matrix indicia that corresponds with the first gauge indica of the first section to be placed on a tooth of the adjacent teeth that is to be restored;

wherein the first dental matrix includes a first section that includes the first matrix indicia, and wherein the first section is configured to be positioned past a biting surface of the tooth in a direction from a gingival end to the biting surface of the tooth when the first dental matrix is placed on the tooth.

* * * * *